(12) United States Patent
Ohishi et al.

(10) Patent No.: US 12,376,758 B2
(45) Date of Patent: Aug. 5, 2025

(54) BIOLOGICAL INFORMATION MONITORING APPARATUS AND MAGNETIC RESONANCE APPARATUS

(71) Applicant: CANON MEDICAL SYSTEMS CORPORATION, Otawara (JP)

(72) Inventors: Takafumi Ohishi, Yokohama (JP); Sadanori Tomiha, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 368 days.

(21) Appl. No.: 17/212,067

(22) Filed: Mar. 25, 2021

(65) Prior Publication Data

US 2021/0298629 A1    Sep. 30, 2021

(30) Foreign Application Priority Data

Mar. 31, 2020    (JP) .................... 2020-063937

(51) Int. Cl.
*A61B 5/055* (2006.01)
*A61B 5/0205* (2006.01)
(Continued)

(52) U.S. Cl.
CPC ............ *A61B 5/055* (2013.01); *A61B 5/0205* (2013.01); *G01R 33/34038* (2013.01); *G01R 33/5612* (2013.01)

(58) Field of Classification Search
CPC ......... A61B 8/483; A61B 8/0883; A61B 8/12; A61B 8/4488; A61B 8/463; A61B 8/467;
(Continued)

(56) References Cited

U.S. PATENT DOCUMENTS 6,011,477 A * 1/2000 Teodorescu .......... A61B 5/0507
340/575
8,489,174 B2 7/2013 Stemmer
(Continued)

FOREIGN PATENT DOCUMENTS

EP    3 708 075 A1    9/2020
JP    2009-55997 A    3/2009
(Continued)

OTHER PUBLICATIONS

European Search Report issued Sep. 1, 2021 in European Patent Application No. 21166197.0, 8 pages.
(Continued)

*Primary Examiner* — Pascal M Bui Pho
*Assistant Examiner* — Neshat Baset
(74) *Attorney, Agent, or Firm* — Oblon, McClelland, Maier & Neustadt, L.L.P.

(57) ABSTRACT

In one embodiment, a biological information monitoring apparatus includes: an antenna assembly including at least one antenna, the antenna assembly being disposed close to an object; a signal generator configured to generate a high-frequency signal; and a displacement detection circuit configured to detect a physical displacement of the object based on the high-frequency signal, wherein the at least one antenna includes: a main antenna to be supplied with the high frequency signal; and a parasitic element to which the high frequency signal is not supplied.

18 Claims, 29 Drawing Sheets

(51) Int. Cl.
*G01R 33/34* (2006.01)
*G01R 33/561* (2006.01)

(58) Field of Classification Search
CPC ..... A61B 8/145; A61B 8/445; G01S 7/52079; G01S 7/52071; G01S 15/8925; G01S 15/8993; G10K 11/34
See application file for complete search history.

(56) References Cited

U.S. PATENT DOCUMENTS

| | | | |
|---|---|---|---|
| 2001/0011964 A1* | 8/2001 | Sadler | H01Q 9/285 343/824 |
| 2005/0206578 A1* | 9/2005 | Ryou | H01Q 5/378 343/895 |
| 2016/0134017 A1* | 5/2016 | Lin | H01Q 5/378 343/861 |
| 2018/0069295 A1* | 3/2018 | Han | H01Q 9/42 |
| 2019/0353722 A1* | 11/2019 | Stormont | G01R 33/3685 |
| 2020/0139138 A1* | 5/2020 | Sit | H04B 5/0031 |
| 2020/0294658 A1 | 9/2020 | Ohishi et al. | |
| 2021/0059555 A1* | 3/2021 | Buchwald | A61B 5/1114 |
| 2021/0322697 A1* | 10/2021 | Ringkamp | A61M 16/024 |

FOREIGN PATENT DOCUMENTS

| | | |
|---|---|---|
| WO | WO 2019/096707 A1 | 5/2019 |
| WO | WO 2019/243213 A1 | 12/2019 |

OTHER PUBLICATIONS

Yong-Jun An, et al., "Sensitivity Enhanced Vital Sign Detection Based on Antenna Reflection Coefficient Variation" IEEE Transactions on Biomedical Circuits and Systems, vol. 10, No. 2, Apr. 2016, pp. 319-327.

Office Action issued Aug. 22, 2023, in corresponding Japanese Patent Application No. 2020-063937, 4 pages.

* cited by examiner

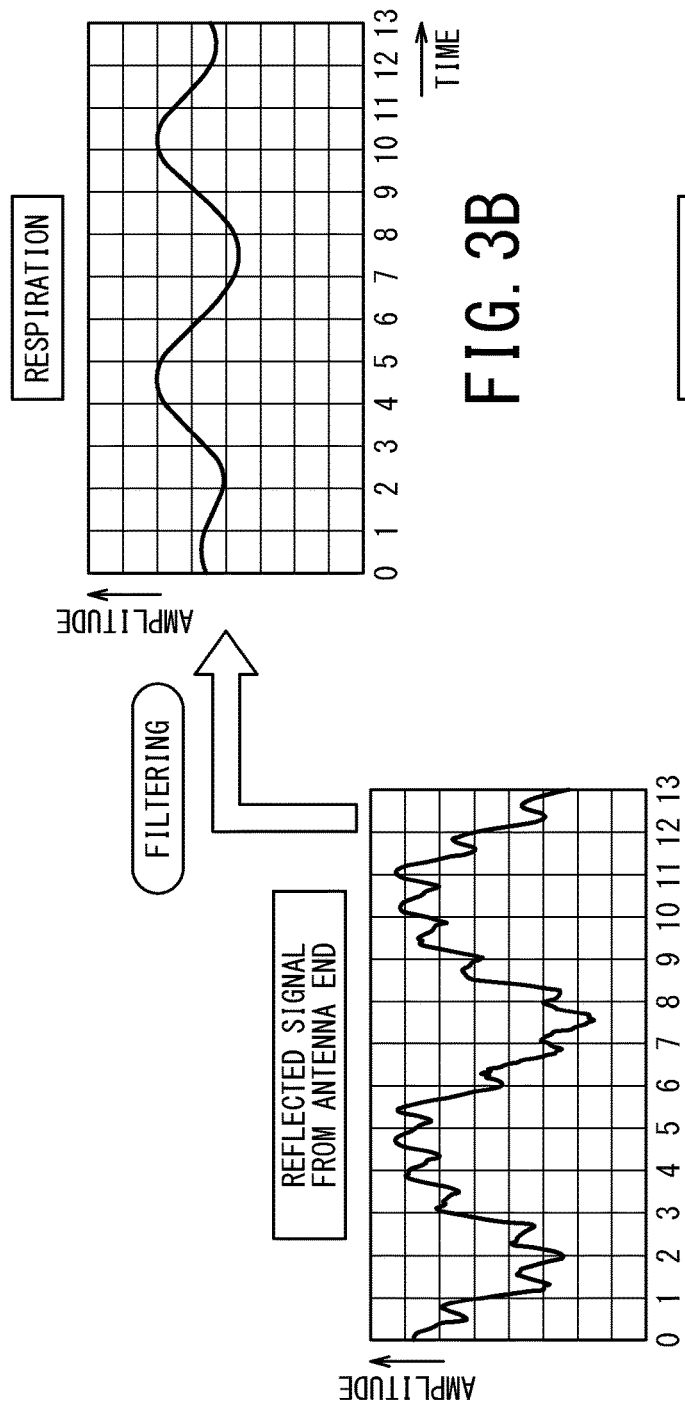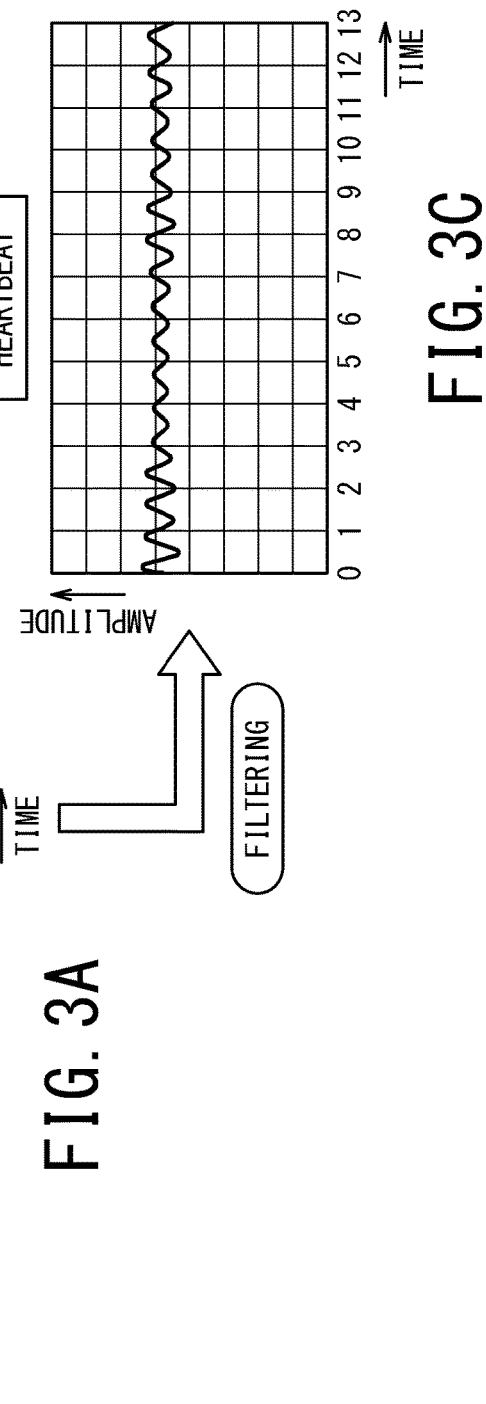

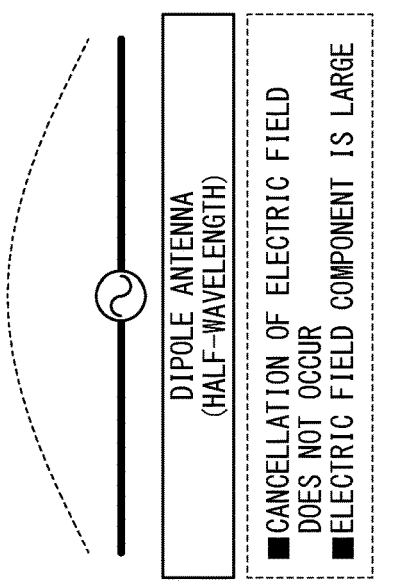

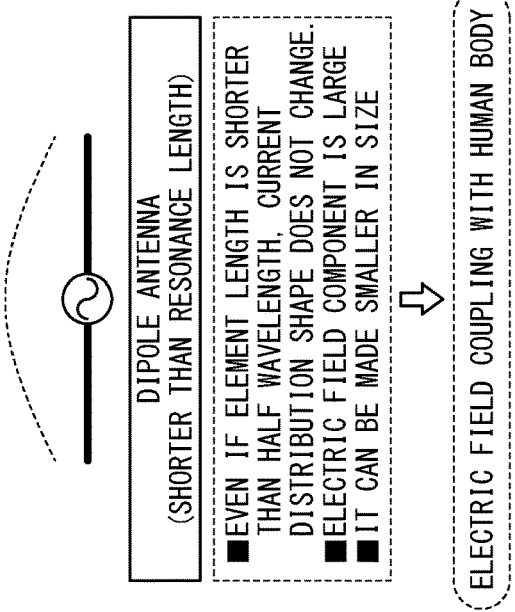

FIG. 4C

DIPOLE ANTENNA (HALF-WAVELENGTH)
- CANCELLATION OF ELECTRIC FIELD DOES NOT OCCUR
- ELECTRIC FIELD COMPONENT IS LARGE

FIG. 4D

DIPOLE ANTENNA (SHORTER THAN RESONANCE LENGTH)
- EVEN IF ELEMENT LENGTH IS SHORTER THAN HALF WAVELENGTH, CURRENT DISTRIBUTION SHAPE DOES NOT CHANGE
- ELECTRIC FIELD COMPONENT IS LARGE
- IT CAN BE MADE SMALLER IN SIZE

⇨ ELECTRIC FIELD COUPLING WITH HUMAN BODY

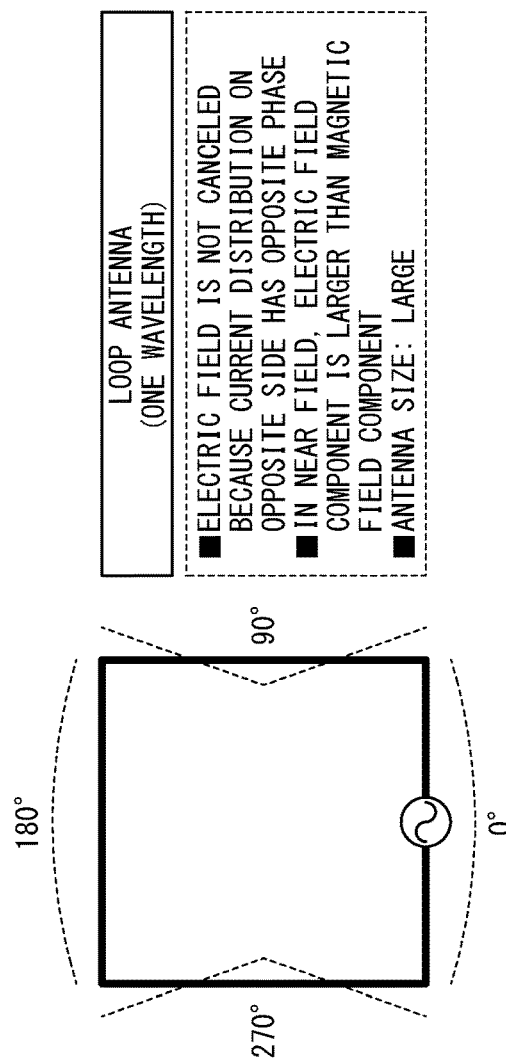

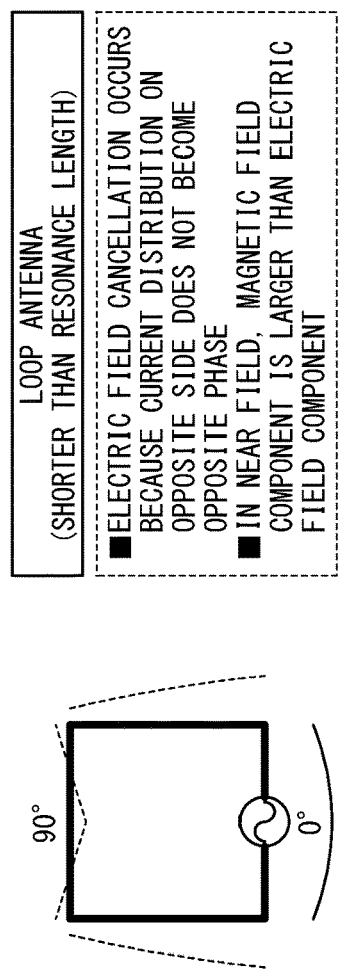

FIG. 4A

LOOP ANTENNA (ONE WAVELENGTH)
- ELECTRIC FIELD IS NOT CANCELED BECAUSE CURRENT DISTRIBUTION ON OPPOSITE SIDE HAS OPPOSITE PHASE
- IN NEAR FIELD, ELECTRIC FIELD COMPONENT IS LARGER THAN MAGNETIC FIELD COMPONENT
- ANTENNA SIZE: LARGE

FIG. 4B

LOOP ANTENNA (SHORTER THAN RESONANCE LENGTH)
- ELECTRIC FIELD CANCELLATION OCCURS BECAUSE CURRENT DISTRIBUTION ON OPPOSITE SIDE DOES NOT BECOME OPPOSITE PHASE
- IN NEAR FIELD, MAGNETIC FIELD COMPONENT IS LARGER THAN ELECTRIC FIELD COMPONENT

⇨ MAGNETIC FIELD COUPLING WITH HUMAN BODY

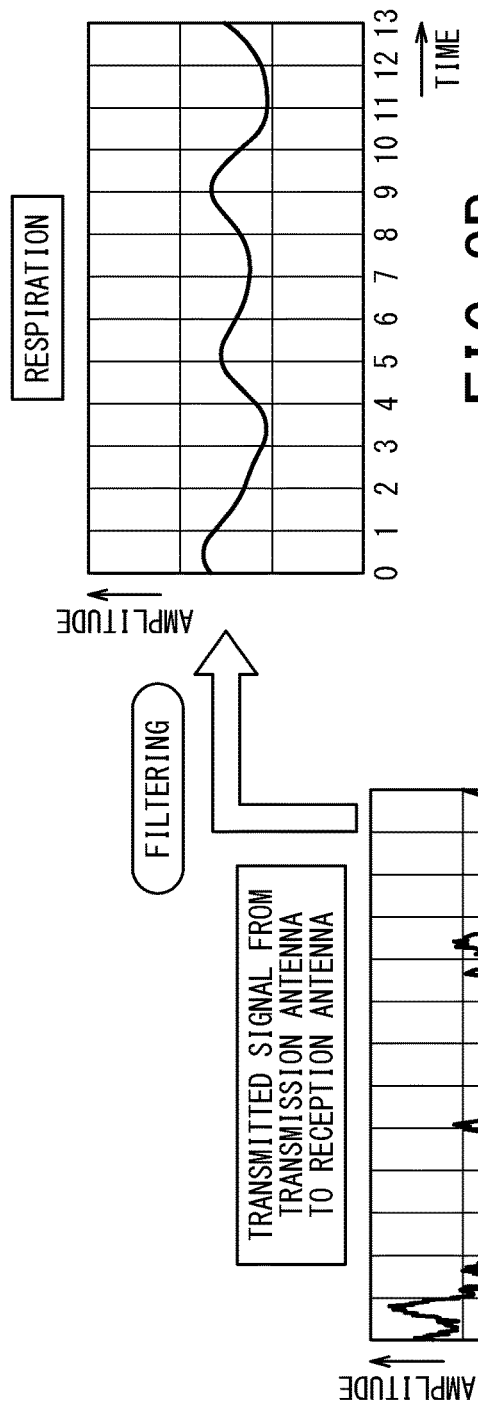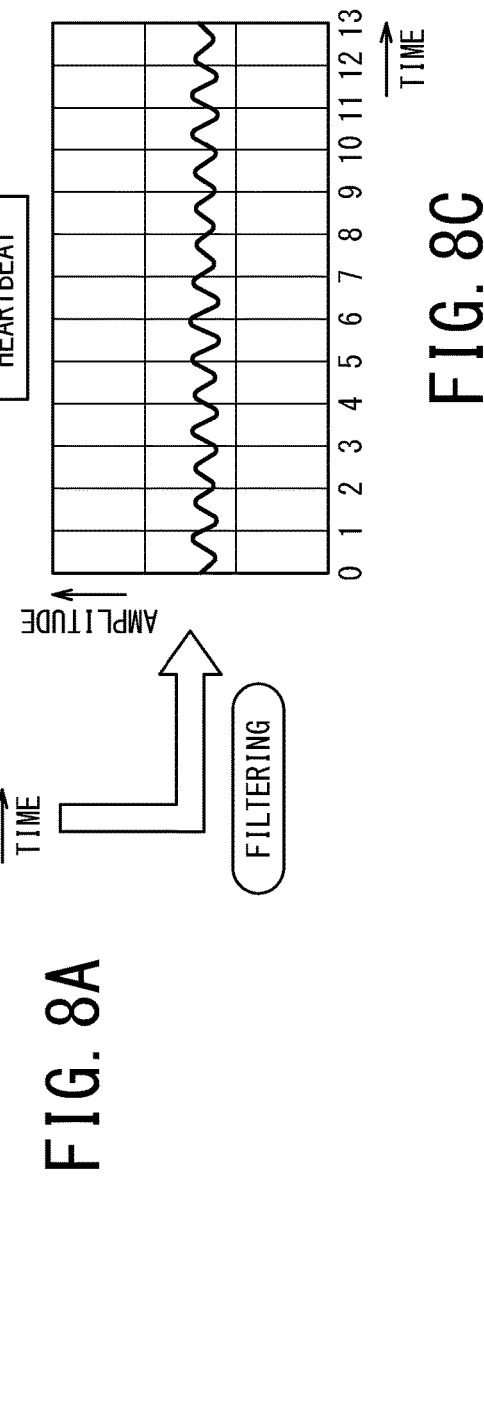

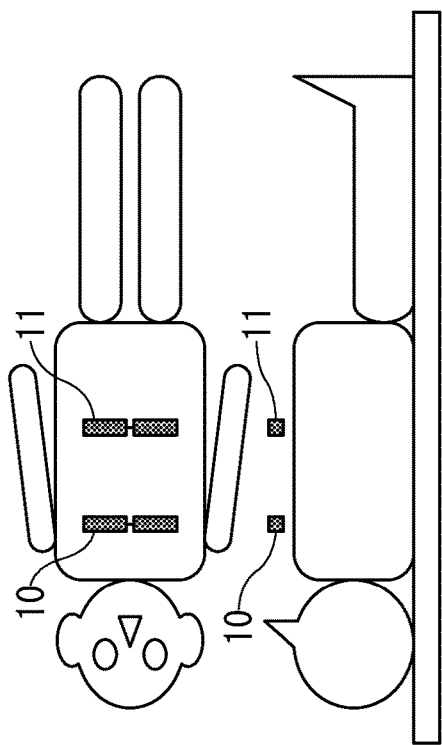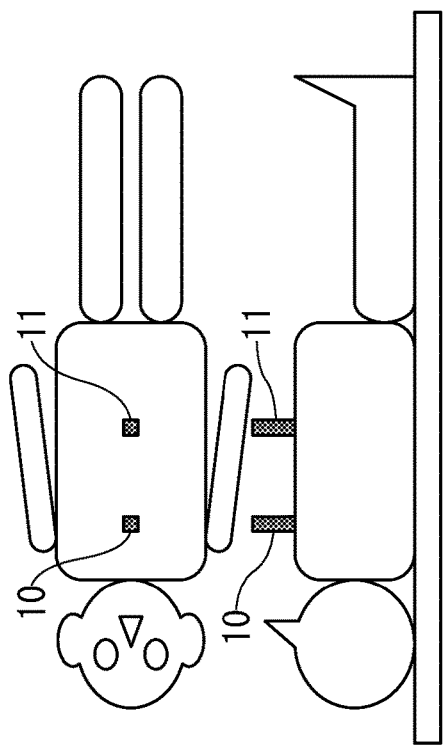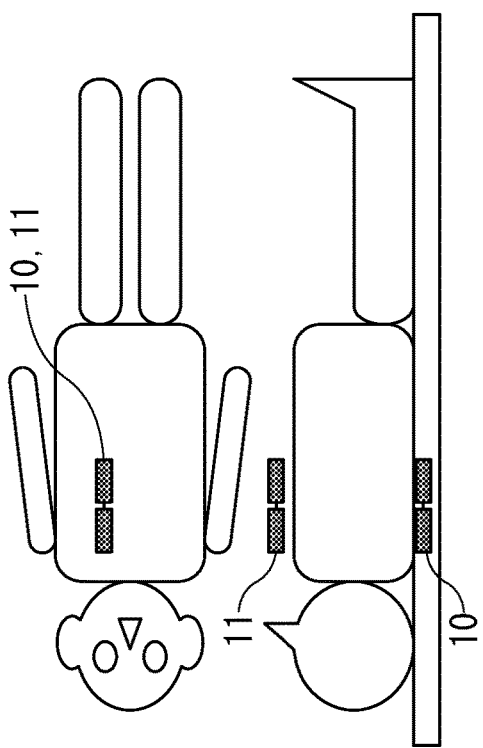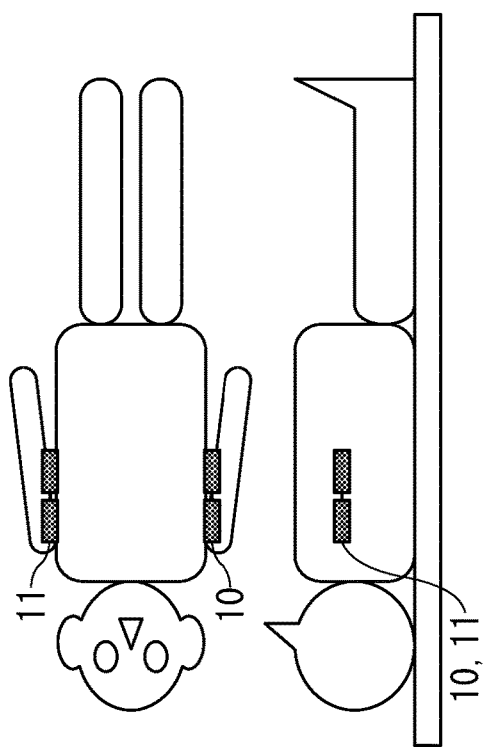

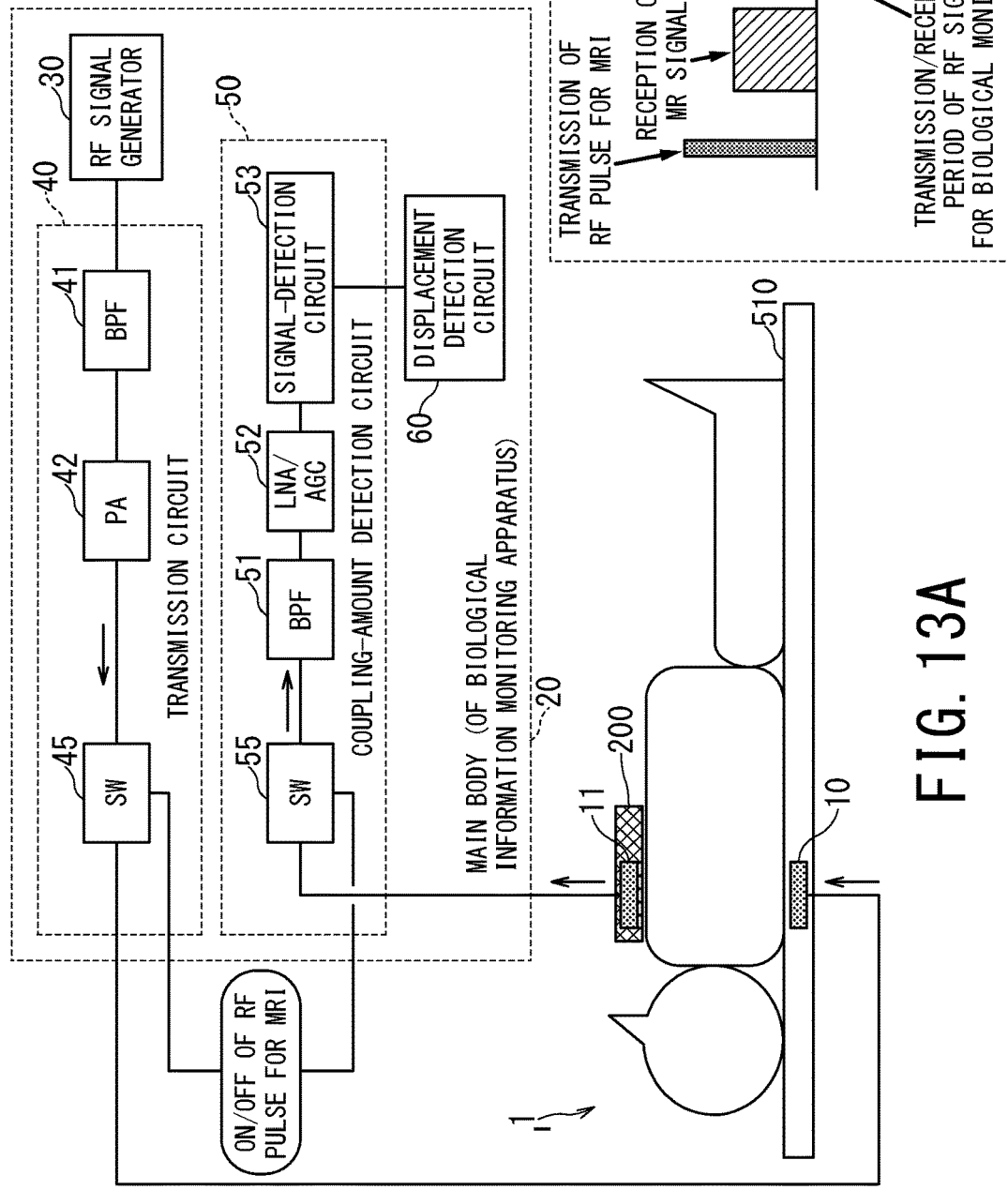

EQUIVALENT CIRCUIT OF CONVENTIONAL ANTENNA

EQUIVALENT CIRCUIT OF ANTENNA OF EMBODIMENT

CONVENTIONAL ANTENNA

ANTENNA OF EMBODIMENT

SMITH CHART OF CONVENTIONAL ANTENNA

SMITH CHART OF ANTENNA OF EMBODIMENT

CONVENTIONAL ANTENNA

ANTENNA OF EMBODIMENT

FREQUENCY CHARACTERISTICS OF CONVENTIONAL ANTENNA

FREQUENCY CHARACTERISTICS OF ANTENNA OF EMBODIMENT

CONVENTIONAL ANTENNA

ANTENNA OF EMBODIMENT

FREQUENCY CHARACTERISTICS OF CONVENTIONAL ANTENNA

FREQUENCY CHARACTERISTICS OF ANTENNA OF EMBODIMENT

CONVENTIONAL ANTENNA

ANTENNA OF EMBODIMENT

FREQUENCY CHARACTERISTICS OF CONVENTIONAL ANTENNA

FREQUENCY CHARACTERISTICS OF ANTENNA OF EMBODIMENT

SMITH CHART OF CONVENTIONAL ANTENNA

SMITH CHART OF ANTENNA OF EMBODIMENT

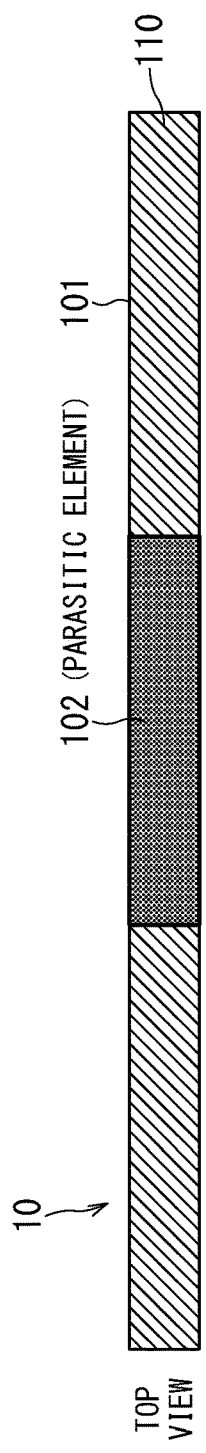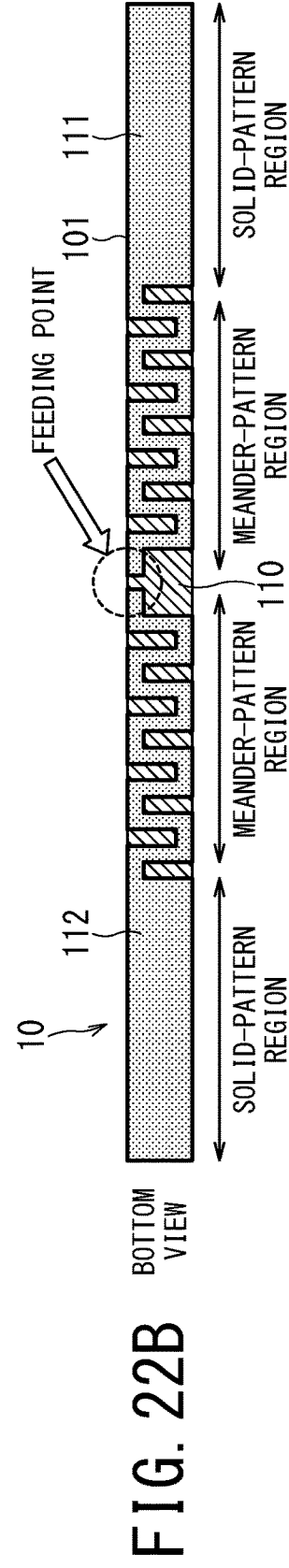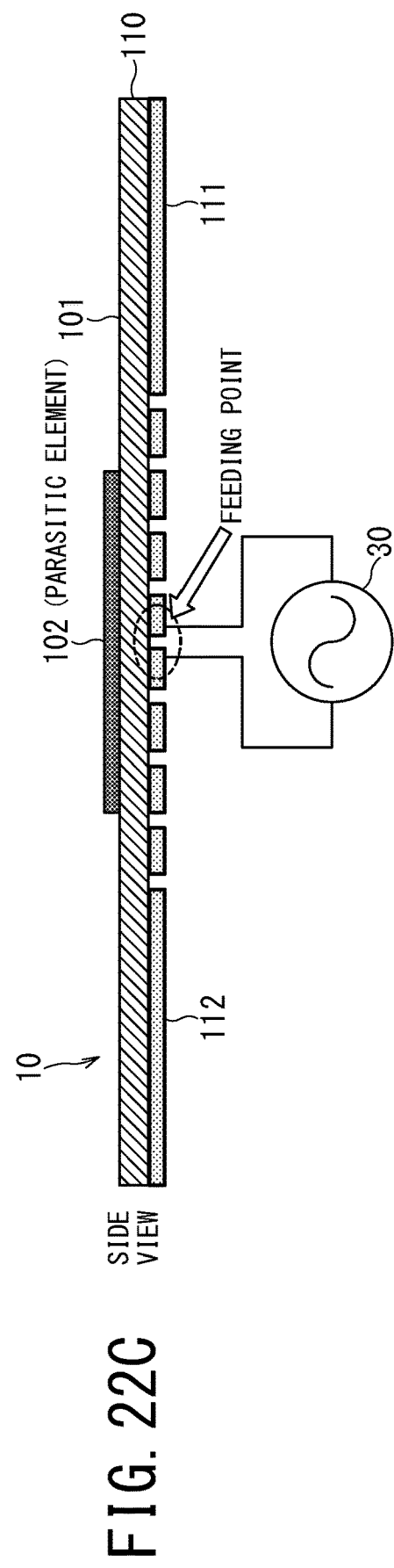

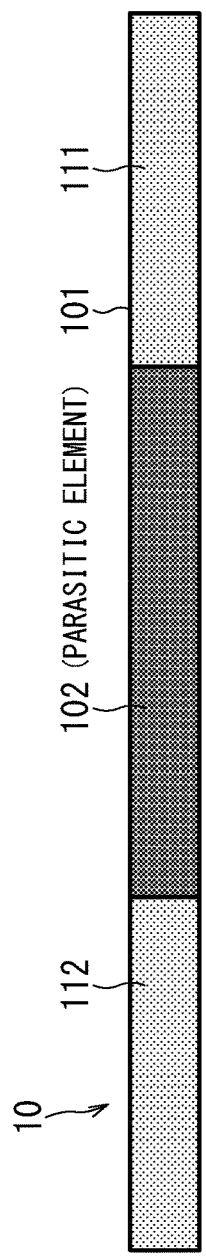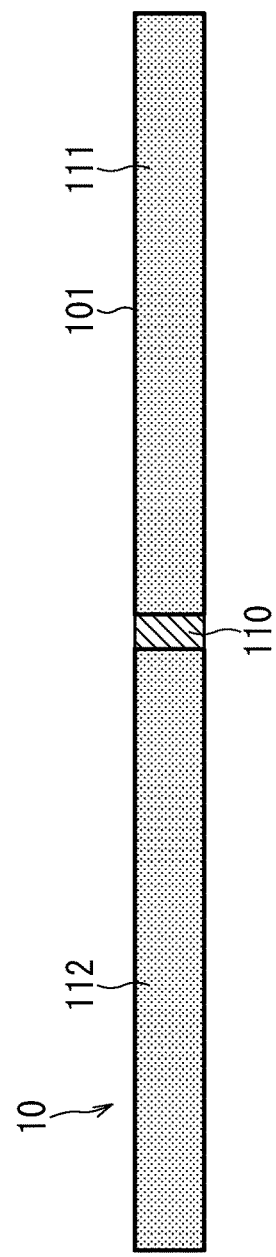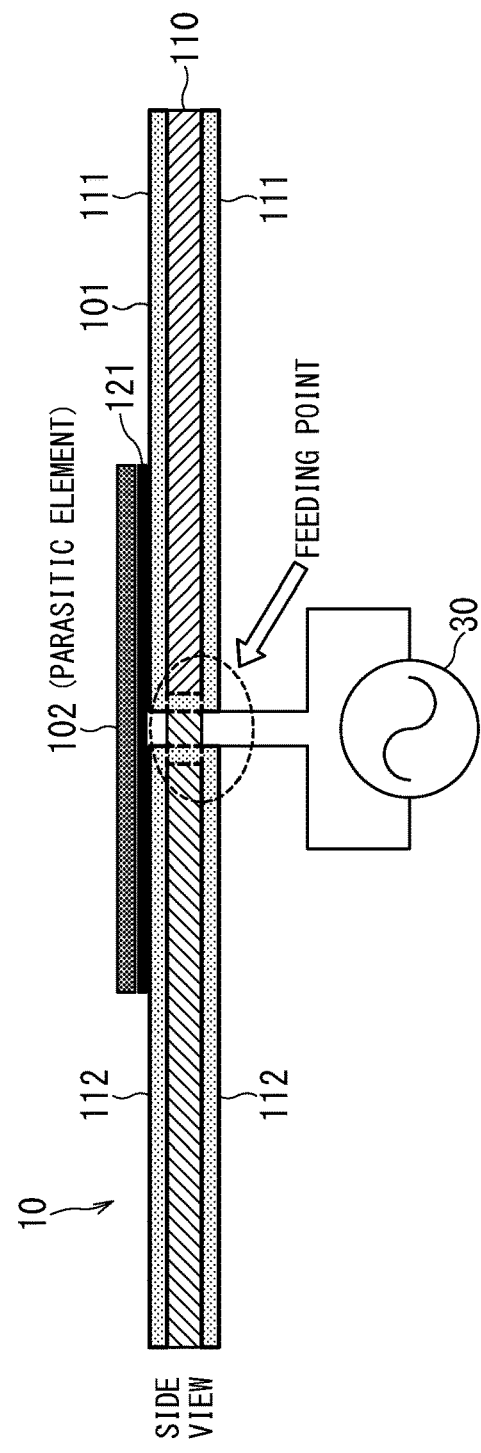

BIOLOGICAL INFORMATION MONITORING APPARATUS AND MAGNETIC RESONANCE APPARATUS

CROSS-REFERENCE TO RELATED APPLICATION

This application is based upon and claims the benefit of priority from Japanese Patent Application No. 2020-063937, filed on Mar. 31, 2020, the entire contents of which are incorporated herein by reference.

FIELD

Disclosed Embodiments relate to a biological information monitoring apparatus and a magnetic resonance apparatus.

BACKGROUND

In imaging using an MRI apparatus, data (e.g., Magnetic Resonance (MR) signals) acquired from an object may fluctuate due to body motion such as heartbeat and respiration of a human body. Conventionally, in order to correct influence of heartbeat on the MR imaging, electrodes of an electrocardiograph, for example, are attached to the human body such that imaging timing is adjusted by using signals outputted from the electrocardiograph and/or the acquired data are corrected on the basis of the signals from the electrocardiograph. However, attaching the electrodes to the human body is a burden on the patient and also causes decrease in work efficiency for a medical imaging technologist.

In another known imaging method, data for monitoring a body motion caused by respiration or breathing are additionally acquired as navigation data aside from data acquisition for generating diagnostic images so that the navigation data can be used for correcting the influence of a body motion caused by respiration. However, in this method, extra time is required for acquiring the navigation data, and thus its imaging time becomes longer. From such a viewpoint, there is a demand for a non-contact type body-motion monitoring apparatus that does not impose a burden on the patient.

The non-contact type body-motion monitoring apparatus has been widely demanded not only in imaging using an MRI apparatus but also in the field of health care. There is also a demand for a body-motion monitoring apparatus that can monitor, for example, a cardiac rate and a respiration rate during sleep and/or during driving of a vehicle in a contactless manner without imposing a burden on the human body.

In a conventionally proposed apparatus, a motion of the object is detected by using a radio wave for detecting a heart rate and/or a respiration rate. In this apparatus, a radio wave is transmitted from an antenna to the object, and then, by detecting change in a reflected radio wave from the object, a motion of the object is detected.

However, in the conventional detection apparatus using a radio wave, not only reflected waves from the object but also reflected waves from various structures around the object are simultaneously received, which causes a fading phenomenon and makes it difficult to reliably and stably detect the heartbeat and respiration of the object.

BRIEF DESCRIPTION OF THE DRAWINGS

In the accompanying drawings:

FIG. 3A is a graph for illustrating actually measured values of a reflected signal from an antenna;

FIG. 3B is a graph for illustrating a waveform of respiration extracted from the reflected signal;

FIG. 3C is a graph for illustrating a waveform of heartbeat extracted from the reflected signal;

FIG. 4A to FIG. 4D are schematic diagrams for illustrating comparison between a loop antenna and a dipole antenna as the antenna to be used in the biological information monitoring apparatus;

FIG. 8A is a graph for illustrating actually measured values of a transmitted signal from the transmission antenna to the reception antenna;

FIG. 8B is a graph for illustrating a waveform of respiration extracted from the transmitted signal;

FIG. 8C is a graph for illustrating a waveform of heartbeat extracted from the transmitted signal;

FIG. 9A to FIG. 9D are schematic diagrams illustrating disposition of the transmission antenna and the reception antenna to be used in the second embodiment;

FIG. 13A is a block diagram illustrating a configuration of the biological information monitoring apparatus to be used in the MRI apparatus;

FIG. 13B is a schematic diagram illustrating a transmission/reception period of a high-frequency signal for a biological monitor;

FIG. 22A to FIG. 22C are schematic views illustrating an appearance and a configuration of a meander antenna as the antenna of the second embodiment;

FIG. 27A to FIG. 27C are schematic views illustrating an appearance and a configuration of the antenna of the third embodiment;

DETAILED DESCRIPTION

In at least one embodiment, an MRI apparatus includes: an antenna assembly including at least one antenna, the antenna assembly being disposed close to an object; a signal generator configured to generate a high-frequency signal; and a displacement detection circuit configured to detect a physical displacement of the object based on the high-frequency signal, wherein the at least one antenna comprises a main antenna to which the high frequency signal is supplied and a parasitic element to which the high frequency signal is not supplied.

First Embodiment

Hereinbelow, the first embodiment of the present invention will be described by referring to the accompanying drawings.

Figure 1:
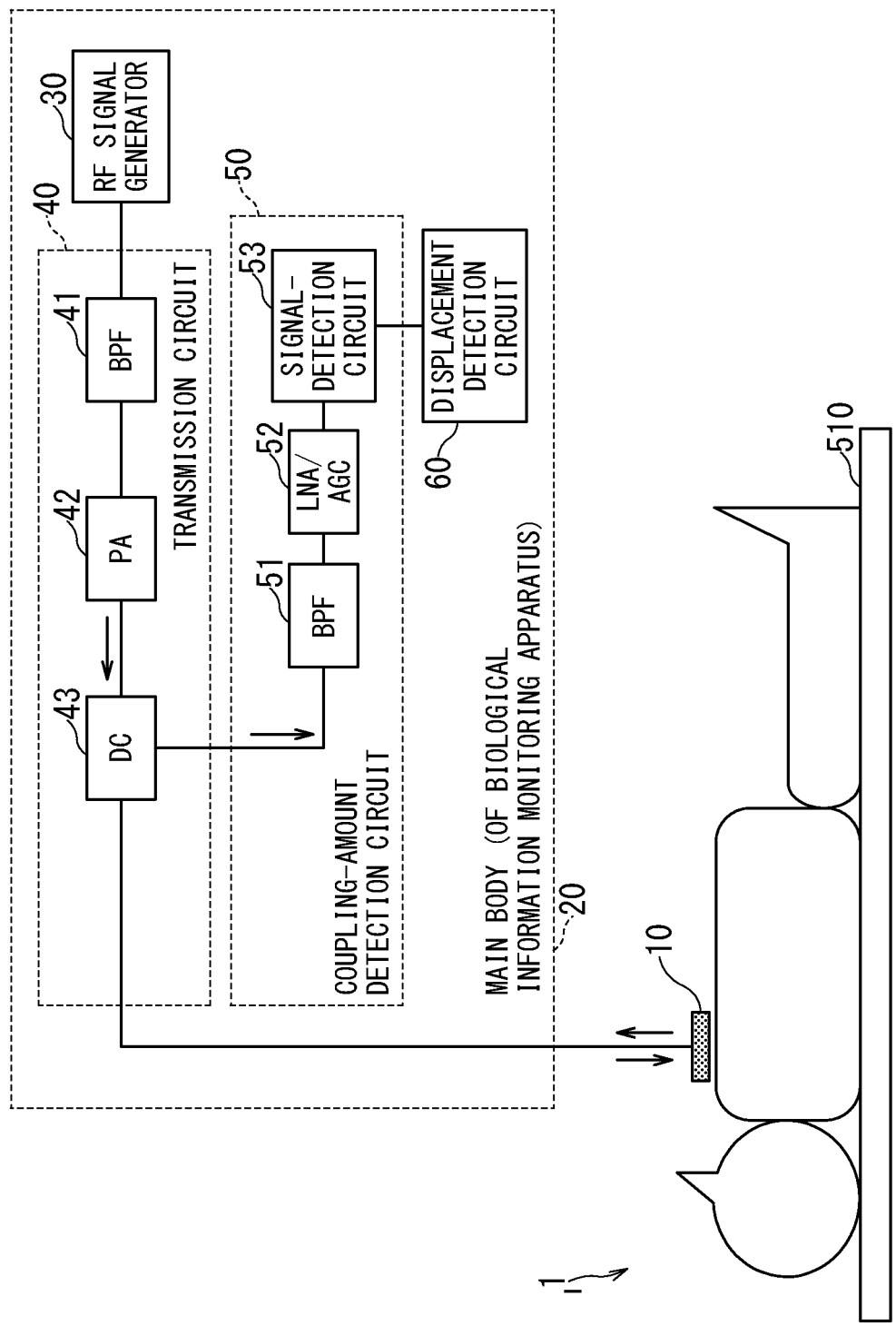
FIG. 1 is a configuration diagram illustrating an overall configuration of a biological information monitoring apparatus according to the first embodiment.

FIG. 1 is a configuration diagram illustrating an overall configuration of a biological information monitoring apparatus 1 according to the first embodiment. The biological information monitoring apparatus 1 includes an antenna 10 and biological-information monitoring main-body 20 (hereinafter, shortly referred to as the main body 20). The antenna 10 is a configuration of an antenna assembly. Since the biological information monitoring apparatus 1 basically includes one antenna in the first embodiment, the antenna assembly is configured as one antenna. In other embodiments described below, the biological information monitoring apparatus 1 may have a plurality of antennas. In such a case, the antenna assembly includes a plurality of antennas.

The antenna 10 is disposed close to an object, which may be usually a human body or a patient. The antenna 10 does not need to be directly adhered to the skin of the object like electrodes of an electrocardiograph, and may be placed on the clothes of the object, for example. Although FIG. 1 illustrates a case where the antenna 10 is disposed on the chest of the object lying on a table 510 of a bed, the posture of the object and/or the part of the object on which the antenna 10 is disposed are not limited to the situation as shown in FIG. 1. For example, the antenna 10 may be disposed on the chest or back of the object in a standing position or may be disposed on the chest or back of the object in a sitting position, for example, during driving of a vehicle.

The main body 20 includes an RF signal generator 30, a transmission circuit 40, a coupling-amount detection circuit 50, and a displacement detection circuit 60.

The RF signal generator (or signal generator, simply) 30 generates a high-frequency signal as a continuous wave. Although the frequency of the high-frequency signal is not limited to a specific frequency, a frequency in the VHF band (from 30 MHz to 300 MHz) or in the UHF band (from 300 MHz to 3 GHz) may be selected in accordance with the dimensions of the antenna, for example. The high-frequency signal may be referred to as a radio-frequency signal.

The transmission circuit 40 causes the high-frequency signal to pass through a band-pass filter (BPF) 41, then amplifies the high-frequency signal to a predetermined power by a power amplifier (PA) 42, and then outputs it to the antenna 10 via a directional coupler (DC) 43.

The coupling-amount detection circuit 50 has the function of detecting the amount of near-field coupling caused by the electric field between the object and the antenna 10. For implementing this function, the coupling-amount detection circuit 50 includes a band-pass filter (BPF) 51, a low-noise amplifier (LNA/AGC) 52 with an automatic gain adjustment function, and a signal-detection circuit 53, for example.

The RF signal generator 30, the transmission circuit 40, and the coupling-amount detection circuit 50 can be mounted on, for example, a printed substrate housed in one casing.

Although the high-frequency signal outputted from the directional coupler 43 of the transmission circuit 40 is inputted to the antenna 10, part of this high-frequency signal does not go into the object but is bounced off (reflected) at the input end of the antenna 10 to be returned to the directional coupler 43, and then is branched and inputted to the coupling-amount detection circuit 50.

The coupling-amount detection circuit 50 detects the signal outputted from the branch end of the directional coupler 43 by using the signal-detection circuit 53 so as to measure magnitude of the reflected signal from the antenna 10. Then, the amount of near-field coupling is detected on the basis of the measured magnitude of the reflected signal, by the coupling-amount detection circuit 50.

Considering that the power outputted from the transmission circuit 40 to the antenna 10 is a constant value, the coupling-amount detection circuit 50 equivalently detects the S11 parameter indicating the reflection loss (i.e., return loss) of the antenna 10.

Figure 2B:
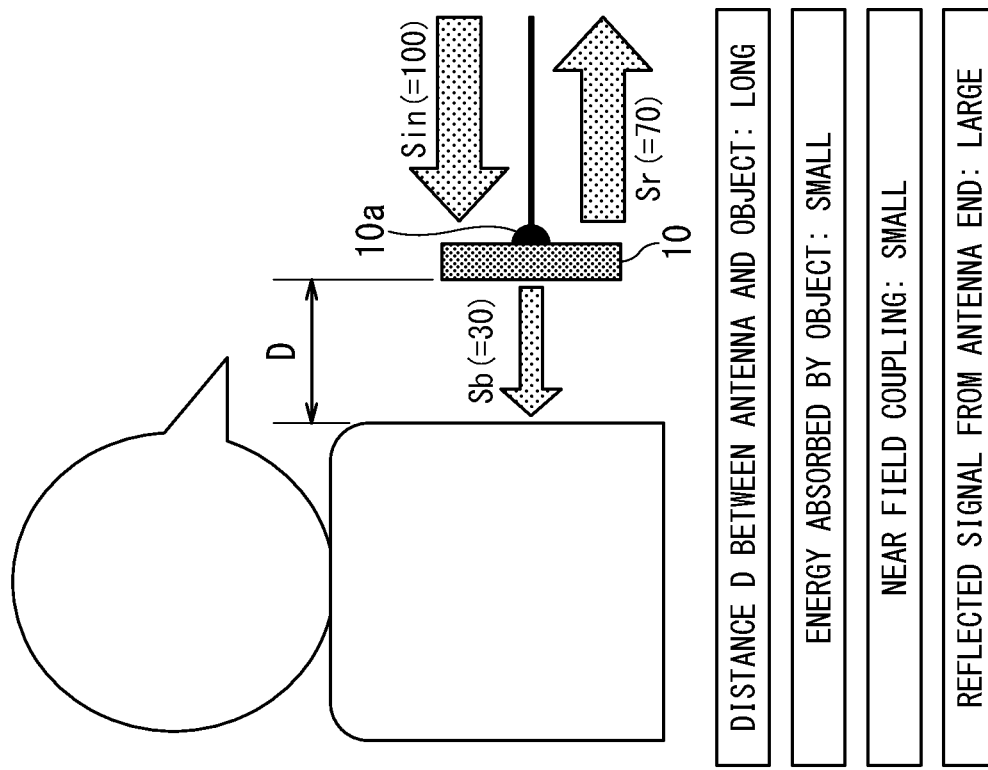
FIG. 2A and FIG. 2B are schematic diagrams illustrating the operation concept of the biological information monitoring apparatus according to the first embodiment.
Figure 2A:
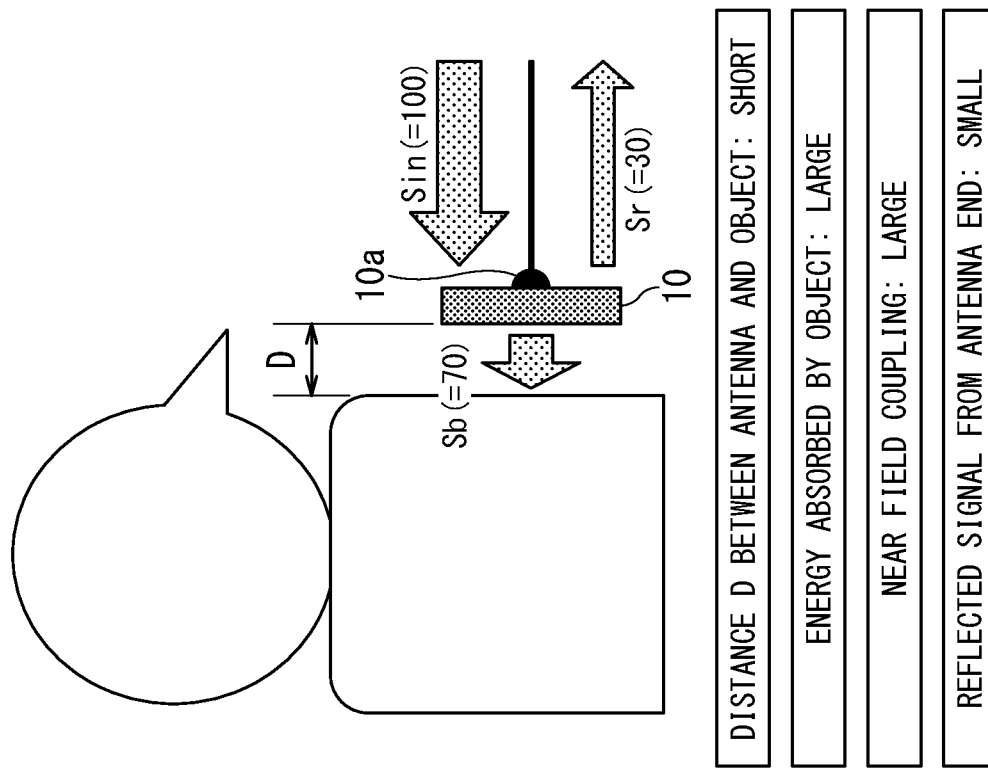

FIG. 2A and FIG. 2B are schematic diagrams illustrating the operation concept of the biological information monitoring apparatus 1 according to the first embodiment. FIG. 2A schematically illustrates the operation when the distance D between the object and the antenna 10 is short, while FIG. 2B schematically illustrates the operation when the distance D between the object and the antenna 10 is long. Note that the object (human body) has electrical conductivity, and thus readily absorbs energy from the antenna 10 when the antenna 10 approaches the object.

Hence, as shown in FIG. 2A, when the distance D between the object and the antenna 10 is short, the energy absorbed by the object increases. This means that the amount of near-field coupling between the object and antenna 10 is large. The power Sin inputted to the antenna 10 is mainly divided into power Sb absorbed by the object and power Sr reflected from the antenna end 10*a* of the antenna 10. When the distance D is short, the power Sb absorbed by the object increases, while the power Sr reflected from the antenna end 10*a* decreases accordingly. For example, when the power Sin inputted to the antenna 10 is assumed to be 100, the power Sb absorbed by the object may become 70, and the power Sr reflected from the antenna end 10*a* may become 30.

This means that the reflected signal from the antenna end 10*a* decreases and the reflection loss (i.e., return loss) of the antenna 10 also decreases when the distance D between the object and the antenna 10 is short. In other words, the S11 parameter, which is an index of the mismatch degree of antenna 10, indicates a small value. The S11 parameter is an index represented by the square root of the ratio of the reflected power to the input power that is inputted to the antenna 10.

On the other hand, as shown in FIG. 2B, when the distance D between the object and the antenna 10 is long, the energy to be absorbed by the object decreases. This means that the amount of near-field coupling between the object and antenna 10 is small. As a result, when the distance D is long, the power Sb absorbed by the object decreases, and thus, the power Sr reflected from the antenna end 10*a* increases, accordingly. For example, when the power Sin inputted to the antenna 10 is assumed to be 100, the power Sb absorbed by the object may become 30, and the power Sr reflected from the antenna end 10*a* may become 70.

This means that the reflected signal from the antenna end 10*a* increases and the reflection loss (i.e., return loss) of the antenna 10 also increases when the distance D between the object and the antenna 10 is long. In other words, the S11 parameter, which is an index of the mismatch degree of antenna 10, indicates a large value.

As described above, when the input power to the antenna 10 is assumed to be constant, the reflected signal from the antenna end 10*a* changes depending on the distance D between the object and the antenna 10. In other words, the mismatch degree of the antenna 10 or the value of the S11 parameter also changes depending on the distance D between the object and the antenna 10. Since the distance D between the object and the antenna 10 changes depending on the body motion such as heartbeat and/or respiration, magnitude of the reflected signal from the antenna end 10*a* or the value of the S11 parameter changes depending on change in body motion such as heartbeat and/or respiration.

The biological information monitoring apparatus 1 of the first embodiment is configured to use above-described characteristics, and detects the magnitude of the reflected signal from the antenna 10 disposed near the object or the value of the S11 parameter so as to detect the body motion such as heartbeat and/or respiration.

FIG. 3A is a graph for illustrating actually measured values of the reflected signal from the antenna 10. In this graph, the horizontal axis indicates time and the vertical axis indicates amplitude of the reflected signal. As shown in FIG. 3A, the reflected signal from the antenna 10 has a waveform in which a short-period fluctuation waveform corresponding to heartbeat is superimposed on a relatively long-period fluctuation waveform corresponding to respiration. The reflected signal from the antenna 10 is detected by the signal-detection circuit 53 of the coupling-amount detection circuit 50, and then is outputted to the displacement detection circuit 60.

The displacement detection circuit 60 may be configured as, for example, a dedicated printed circuit board provided with a processor or may be configured as an information processing apparatus such as a personal computer or a tablet terminal device provided with a display.

The displacement detection circuit 60 performs filtering processing for extracting a frequency component corresponding to a respiratory motion and another frequency component corresponding to heartbeat on the reflected signal detected by the signal-detection circuit 53 so as to generate a respiratory waveform shown in FIG. 3B and a heartbeat waveform shown in FIG. 3C. Additionally or alternatively, the displacement detection circuit 60 may perform Fourier transform on the reflected signal from the antenna 10, then extract the respective frequency components corresponding to the respiratory motion and heartbeat on a frequency space, and then perform inverse Fourier transform on both extracted frequency components so as to generate the respiratory waveform shown in FIG. 3B and the heartbeat waveform shown in FIG. 3C.

The displacement detection circuit 60 may cause an appropriate display to display the generated respiratory waveform and heartbeat waveform, or may analyze the generated respiratory waveform and heartbeat waveform. For example, the displacement detection circuit 60 may analyze the respiratory waveform and/or the heartbeat waveform so as to acquire respiratory and/or cardiac parameters such as a respiratory rate, a respiratory cycle, a cardiac rate, and/or a cardiac cycle. Further, the displacement detection circuit 60 may detect presence/absence of an abnormality in respiration or heartbeat from the acquired respiratory and/or cardiac parameters.

FIG. 4A to FIG. 4D are schematic diagrams for illustrating comparison between a loop antenna and a dipole antenna as the antenna 10 used in the biological information monitoring apparatus 1.

FIG. 4A shows a loop antenna having a loop length of a resonance length, i.e., a one-wavelength loop antenna. In the one-wavelength loop antenna, the electric field is not canceled because the current distribution on the opposite side has an opposite phase. Thus, in the near field, the electric field component becomes larger than the magnetic field component. Although it depends on the frequency to be used, the one-wavelength loop antenna is relatively large in antenna size.

FIG. 4B shows a loop antenna, and a loop length of which is shorter than the resonance length. In this type of loop antenna, cancellation of the electric field occurs because the current distribution on the opposite side does not become the opposite phase. Thus, in the near field, the magnetic field component becomes larger than the electric field component. Hence, coupling with the human body in the near field is magnetic field coupling. Magnetic field coupling tends to readily pass through the interior of the human body.

FIG. 4C shows a half-wave dipole antenna. In the half-wavelength dipole antenna, there is no cancellation of the electric field, and thus, the electric field component is large in the near field.

FIG. 4D shows a dipole antenna, and an element length of which is shorter than the resonance length. Even when the element length is shorter than the resonance length (i.e., half wavelength), the current distribution shape does not change. Thus, in the case of this dipole antenna shown in FIG. 4D, the electric field component is large in the near field similarly to the half-wave dipole antenna. The dipole antenna shown in FIG. 4D can be made smaller in size than a half-wave dipole antenna. In the case of this dipole antenna, the electric field component is large in the near field, and thus coupling with the human body in the near field is electric field coupling. Electric field coupling tends to readily propagate on the surface of the body.

From the viewpoint of miniaturization, it is preferred to use a loop antenna having a loop length shorter than the resonance length (FIG. 4B) and/or a dipole antenna (having an element length) shorter than a half wavelength (FIG. 4D), and any one of these two antennas can be used for the biological information monitoring apparatus 1. However, it is recognized that the dipole antenna tends to extract a more detailed electrocardiographic waveform than the loop antenna.

In a usual antenna used for communication, it is required that the reflected signal from the antenna is reduced as much as possible so that the power going out into space is increased as much as possible. Thus, it is considered that the voltage standing wave ratio (VSWR) of the antenna is preferably as close to 1.0 as possible. By contrast, in the biological information monitoring apparatus 1 of the first embodiment, heartbeat and a respiratory motion are detected by detecting the reflected signal from the antenna 10. For this reason, having a reflected signal from the antenna 10 to some extent is actually preferable. Hence, the voltage standing wave ratio (VSWR) of the antenna 10 used in the biological information monitoring apparatus 1 of the first embodiment is preferably set to, for example, a value between 2.0 and 5.0.

FIG. 5A to FIG. 5D are schematic diagrams for illustrating disposition of the antenna 10 used in the first embodiment. Although the number of the antenna 10 of the first embodiment is basically one, many variations are conceivable for disposition and orientation of the antenna 10. As a basic idea, it is preferred to dispose the antenna 10 at a position where the body motion is more apparent to tell. In the case of detecting heartbeat, it is preferred to dispose the antenna 10 at a position as close to the heart as possible.

Figure 5A:
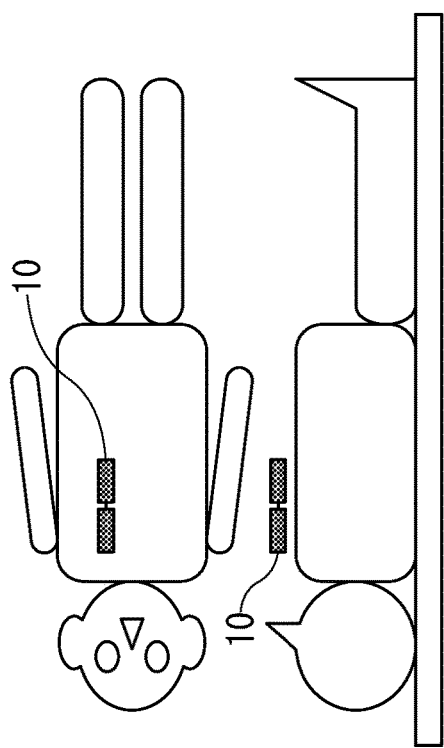
FIG. 5A to FIG. 5D are schematic diagrams for illustrating disposition of the antenna to be used in the first embodiment.
Figure 5B:
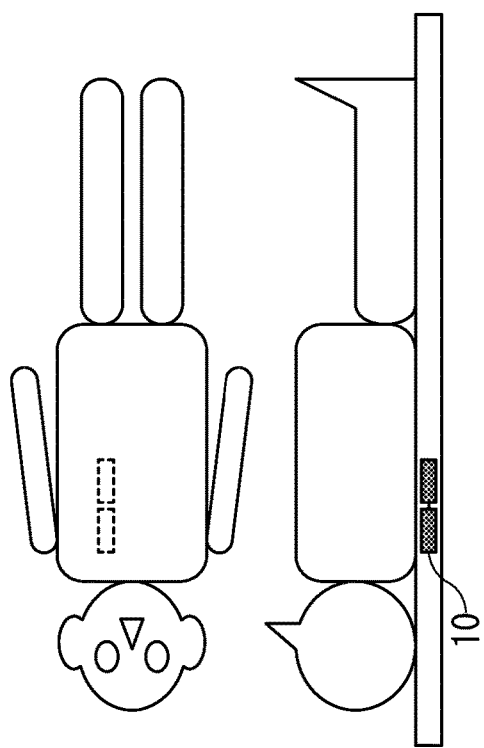

Each of FIG. 5A to FIG. 5D illustrates a dipole antenna as the antenna 10. It is said that the heart moves more in the head-foot direction than in the right-left direction of the object. For this reason, in FIG. 5A, the antenna 10 is disposed in longitudinal direction that matches the head-foot direction of the object, and near the heart on the anterior side in the anterior-posterior direction of the object. In FIG. 5B, the antenna 10 is disposed near the heart on the back side (i.e., posterior side) of the object, while the longitudinal direction of the dipole antenna matches the head-foot direction of the object as well.

Figure 5C:
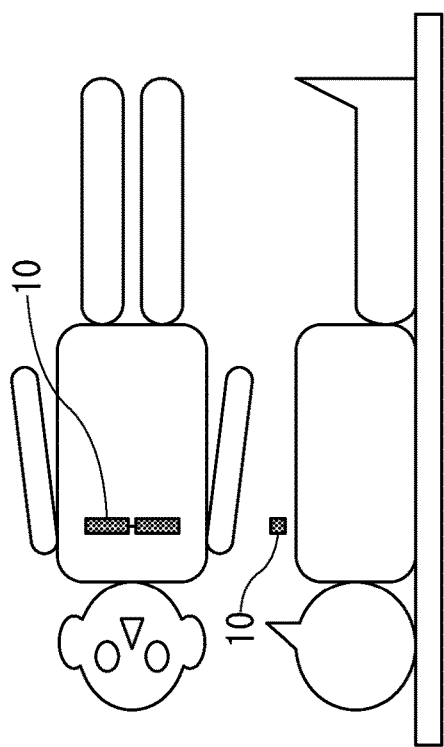
Figure 5D:
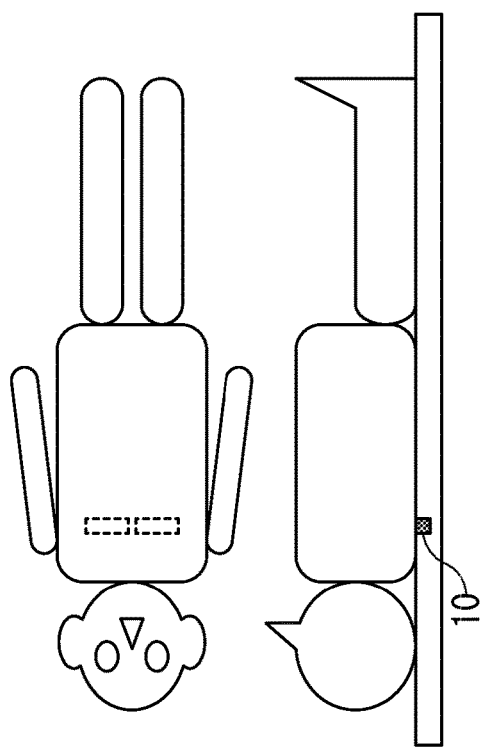

The position of the antenna 10 may be subject to some physical restrictions. For example, when the cardiac rate of the object is measured by using the biological information monitoring apparatus 1 during imaging of the object using an MRI apparatus 100, an RF coil (i.e., local coil or surface coil) 200 of the MRI apparatus 100 is disposed on the object. When the RF coil 200 is a chest coil, for example, the antenna 10 is disposed at a position avoiding the chest coil and as close to the heart as possible, as shown in FIG. 5C. When the antenna 10 is disposed on the back side and the RF coil 200 is a spine coil, for example, the antenna 10 is disposed at a position avoiding the spine coil and as close to the heart as possible, as shown in FIG. 5D.

As described above, in the biological information monitoring apparatus 1 according to the first embodiment, a body motion such as heartbeat and/or respiration is detected as change in coupling amount of the near-field coupling between the antenna 10 and the human body. This change in coupling amount of the near-field coupling is measured as change in the reflected signal reflected from the input end of the antenna 10 or as change in the value of the S11 parameter, which is the reflection loss of the antenna 10. The "input end" of the antenna 10 may be referred to as an "input terminal" of the antenna 10. Thus, while the detection method of the biological information monitoring apparatus 1 according to the first embodiment is a non-contact detection method using radio waves, the biological information monitoring apparatus 1 is less susceptible to fading due to interference with reflected waves from structures around the object, for example, a gantry structure of an MRI apparatus or various devices in an examination room. Thus, the biological information monitoring apparatus 1 can detect heartbeat and/or a respiratory motion with high reliability.

Second Embodiment

Figure 6:
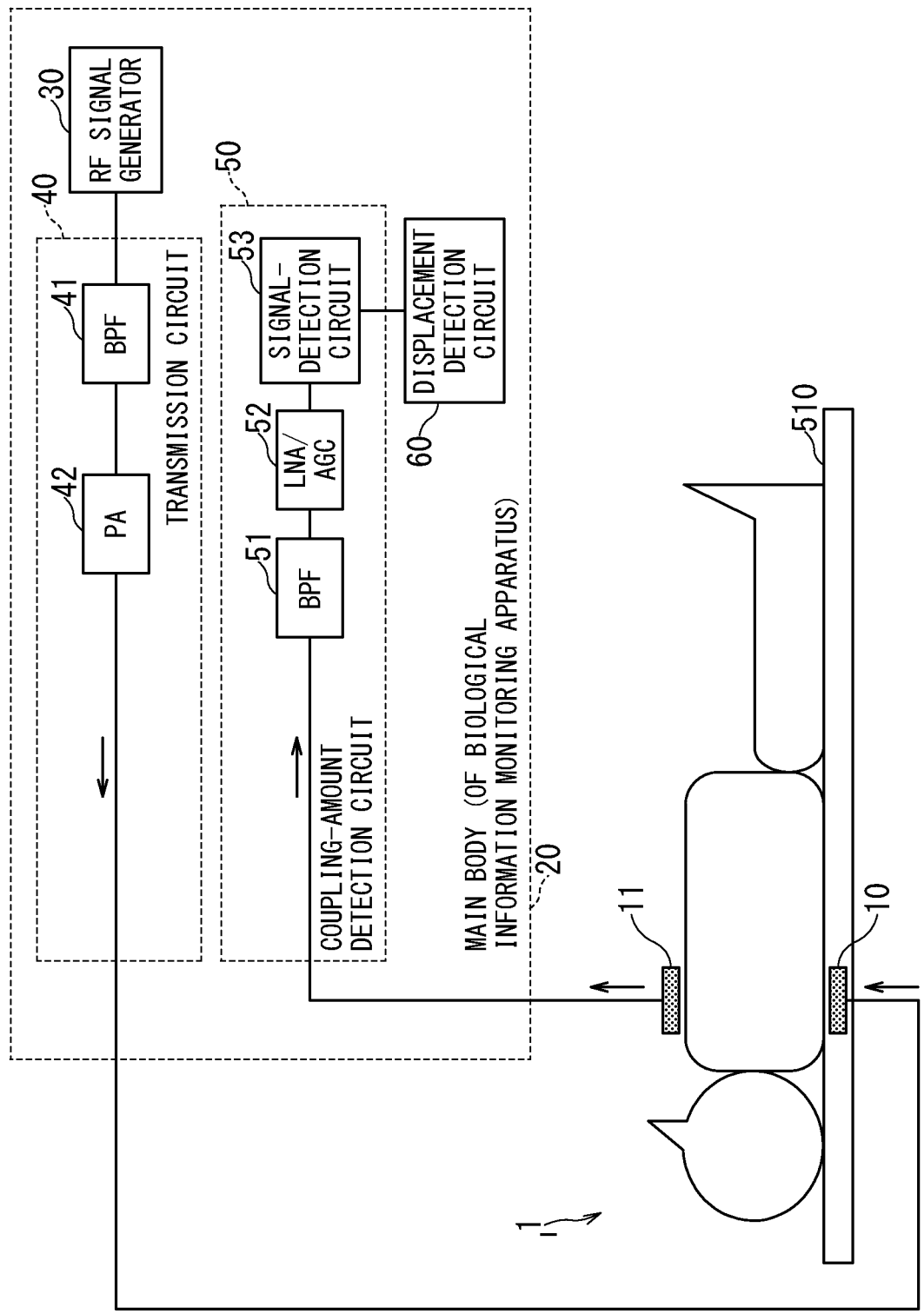
FIG. 6 is a block diagram illustrating an overall configuration of the biological information monitoring apparatus according to the second embodiment.

FIG. 6 is a block diagram illustrating an overall configuration of the biological information monitoring apparatus 1 according to the second embodiment. The biological information monitoring apparatus 1 of the first embodiment is provided with only one antenna 10 in principle, whereas the biological information monitoring apparatus 1 of the second embodiment is provided with at least two antennas including a transmission antenna (first antenna) 10 and a reception antenna (second antenna) 11.

As to configuration of the main body 20 (i.e., biological-information-monitoring main-body 20), the second embodiment is almost the same as the first embodiment, and the main body 20 in the second embodiment includes the RF signal generator 30, the transmission circuit 40, the coupling-amount detection circuit 50, and the displacement detection circuit 60.

The main body 20 in the second embodiment differs from the first embodiment in that the transmission circuit 20 in the second embodiment does not include the directional coupler (DC) 43. The power amplifier (PA) 42 of the transmission circuit 20 and the transmission antenna 10 are directly connected without passing through the directional coupler (DC) 43. The band-pass filter (BPF) 51 of the coupling-amount detection circuit 50 and the reception antenna 11 are also directly connected without passing through the directional coupler (DC) 43.

The coupling-amount detection circuit 50 of the second embodiment uses the signal-detection circuit 53 for detecting the transmitted signal, which is originally the high-frequency signal outputted from the RF signal generator 30, and is transmitted from the transmission antenna 10 through the object to the reception antenna 11, and detects the amount of near-field coupling on the basis of magnitude of the transmitted signal.

Considering that the power outputted from the transmission circuit 40 to the transmission antenna 10 is a constant value, the coupling-amount detection circuit 50 equivalently detects the S21 parameter indicating the insertion loss from the transmission antenna 10 to the reception antenna 11.

Figure 7B:
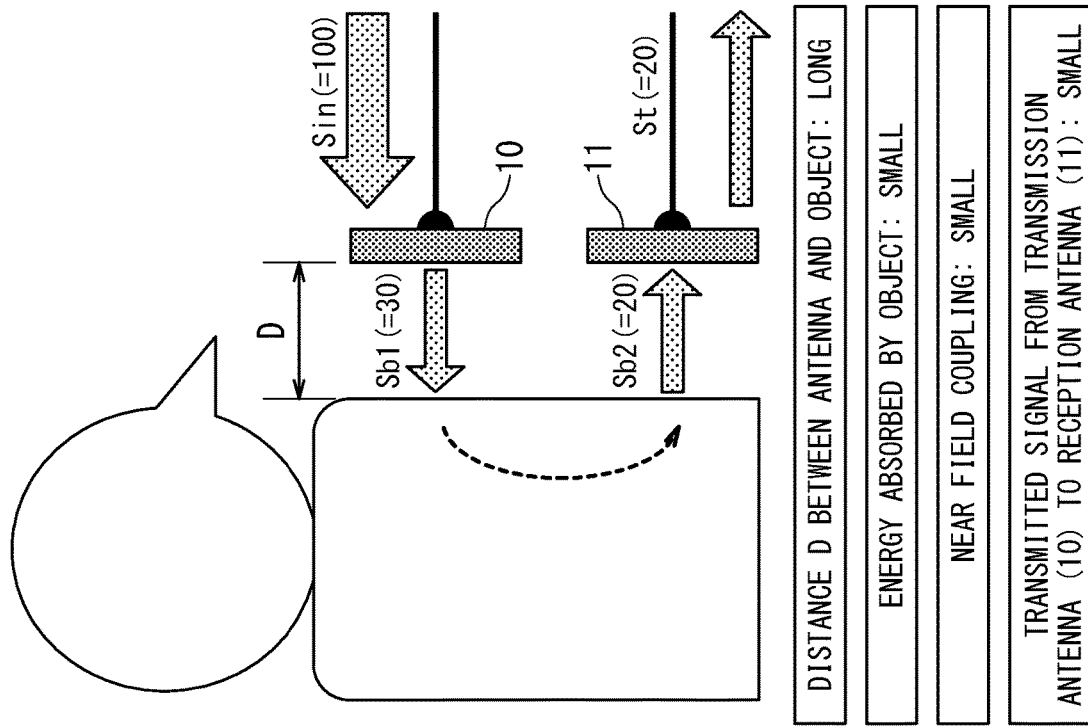
FIG. 7A and FIG. 7B are schematic diagrams illustrating the operation concept of the biological information monitoring apparatus according to the second embodiment.
Figure 7A:
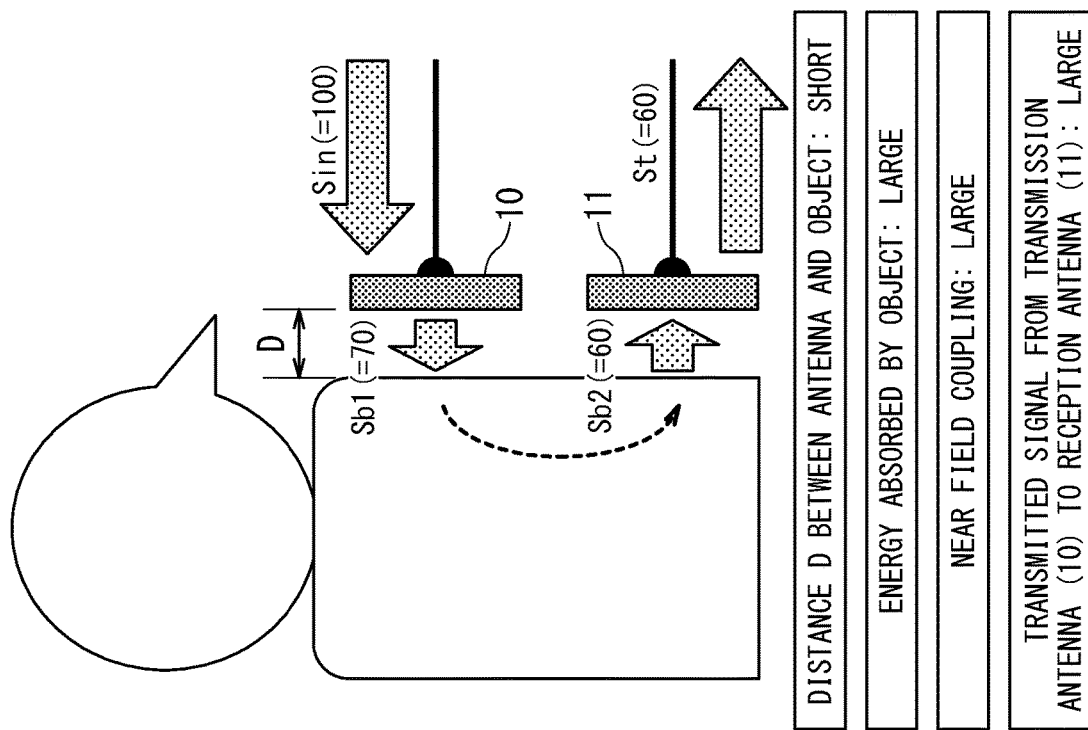

FIG. 7A and FIG. 7B are schematic diagrams illustrating the operation concept of the biological information monitoring apparatus 1 according to the second embodiment. FIG. 7A schematically illustrates the operation when the distance D between the object and the antenna 10 is short, while FIG. 7B schematically illustrates the operation when the distance D between the object and the antenna 10 is long. As mentioned above, the object (human body) has electrical conductivity. Thus, when the distance between the transmission antenna 10 and the object is short, the object (human body) more readily absorbs the energy from the transmission antenna 10. Hence, the energy absorbed from the transmission antenna 10 into the object increases. This means that the coupling amount of the near-field coupling between the object and the transmission antenna 10 is large.

Similarly, when the reception antenna 11 approaches the object, the energy inputted from the object to the reception antenna 11 also increases, and this means that the coupling amount of the near-field coupling between the object and the reception antenna 11 is large. The power Sin inputted to the antenna 10 is absorbed by the object as the power Sb1, propagates the interior and the surface of the object, and is transmitted to the reception antenna 11 as the power Sb2. When the distance D is short, the power Sb1 absorbed from the transmission antenna 10 to the object increases, and accordingly, the power Sb2 emitted from the object to the input antenna 11 increases. For example, when the power Sin inputted to the transmission antenna 10 is assumed to be 100, the power Sb absorbed by the object from the transmission antenna 10 may be 70, and the power Sb2 emitted from the object to the reception antenna 11 may be 60, and thus the power St exiting from the reception antenna 11 is also 60.

This means that the transmitted signal from the transmission antenna 10 to the reception antenna 11 increases and the insertion loss from the transmission antenna 10 to the reception antenna 11 decreases, when the distance D between the object and the transmission antenna 10/the reception antenna 11 is short. In other words, the S21 parameter (when expressed as an antilogarithm value), which is an index of the insertion loss from the transmission antenna 10 to the reception antenna 11, shows a large value.

On the other hand, as shown in FIG. 7B, when the distance D between the transmission antenna 10 and the object increases, the object becomes less likely to absorb the energy from the transmission antenna 10. Thus, the energy absorbed by the object from the transmission antenna 10 decreases. This means that the amount of near-field coupling between the object and the reception antenna 11 is reduced. Similarly, when the distance D between the reception antenna 11 and the object increases, the energy inputted from the object to the reception antenna 11 also decreases. This means that the amount of near-field coupling between the object and the reception antenna 11 is also reduced. For example, when the power Sin inputted to the transmission antenna 10 is assumed to be 100, the power Sb absorbed by the object from the transmission antenna 10 may become 30, and the power Sb2 emitted from the object to the reception antenna 11 may become 20, and thus, the power St exiting from the reception antenna 11 becomes also 20.

This means that the transmitted signal from the transmission antenna 10 to the reception antenna 11 decreases and the insertion loss from the transmission antenna 10 to the reception antenna 11 increases when the distance D between the object and the transmission antenna 10/the reception antenna 11 is long. In other words, the S21 parameter (when expressed as an antilogarithm value), which is an index of the insertion loss from the transmission antenna 10 to the reception antenna 11, shows a small value.

FIG. 8A is a graph for illustrating actually measured values of a transmitted signal from the transmission antenna 10 to the reception antenna 11. In this graph, the horizontal axis indicates time and the vertical axis indicates amplitude of the transmitted signal. The transmitted signal in the second embodiment is similar to the reflected signal (FIG. 3A) in the first embodiment and has a waveform in which a short-period fluctuation waveform corresponding to heartbeat is superimposed on a relatively long-period fluctuation waveform corresponding to respiration. This transmitted signal is also detected by the signal-detection circuit 53 of the coupling-amount detection circuit 50 and then is outputted to the displacement detection circuit 60.

The displacement detection circuit 60 performs filtering processing and/or Fourier transform processing on the reflected signal detected by the signal-detection circuit 53 so as to extract the respective two frequency components corresponding to the respiratory motion and heartbeat, and then generates a respiratory waveform shown in FIG. 8B and a heartbeat waveform shown in FIG. 8C in a manner similar to the first embodiment.

FIG. 9A to FIG. 9D are schematic diagrams illustrating disposition of the transmission antenna 10 and the reception antenna 11 used in the biological information monitoring apparatus 1 of the second embodiment. Many variations are conceivable for disposition and orientation of the transmission antenna 10 and the reception antenna 11 of the second embodiment. As a basic idea, the transmission antenna 10 and the reception antenna 11 are desirably disposed so as to sandwich the body part where the body motion is more apparent to tell. For example, in the case of detecting heartbeat, the transmission antenna 10 and the reception antenna 11 are desirably disposed so as to sandwich the heart in any one of the anterior-posterior direction, the right-left direction, and the head-foot direction of the object.

Each of FIG. 9A, FIG. 9B, and FIG. 9C illustrates a dipole antenna, and FIG. 9D illustrates a monopole antenna. FIG. 9A shows a disposition example in which the heart of the object is sandwiched between the transmission antenna 10 and the reception antenna 11 in the anterior-posterior direction.

FIG. 9B shows another disposition example in which the heart of the object is sandwiched between the transmission antenna 10 and the reception antenna 11 in the right-left direction.

FIG. 9C shows yet another disposition example in which the heart of the object is sandwiched between the transmission antenna 10 and the reception antenna 11 in the head-foot direction.

Meanwhile, FIG. 9D shows a disposition aspect in which the heart of the object is sandwiched between the transmission antenna 10 and the reception antenna 11, each of which is configured as a monopole antenna, in the head-foot direction.

Note that, there is no particular need to distinguish between the transmission antenna 10 and the reception antenna 11. In any of the disposition examples of FIG. 9A to FIG. 9D, the respective position of the transmission antenna 10 and reception antenna 11 can be interchanged.

The voltage standing wave ratio (VSWR) of the transmission antenna 10 used in the biological information monitoring apparatus 1 of the second embodiment is preferably set to, for example, a value between 2.0 and 5.0 similarly to the first embodiment. By contrast, as for the reception antenna 11, lower VSWR is preferred, for example, a VSWR of 2.0 or less is preferred.

Third Embodiment

Figure 10:
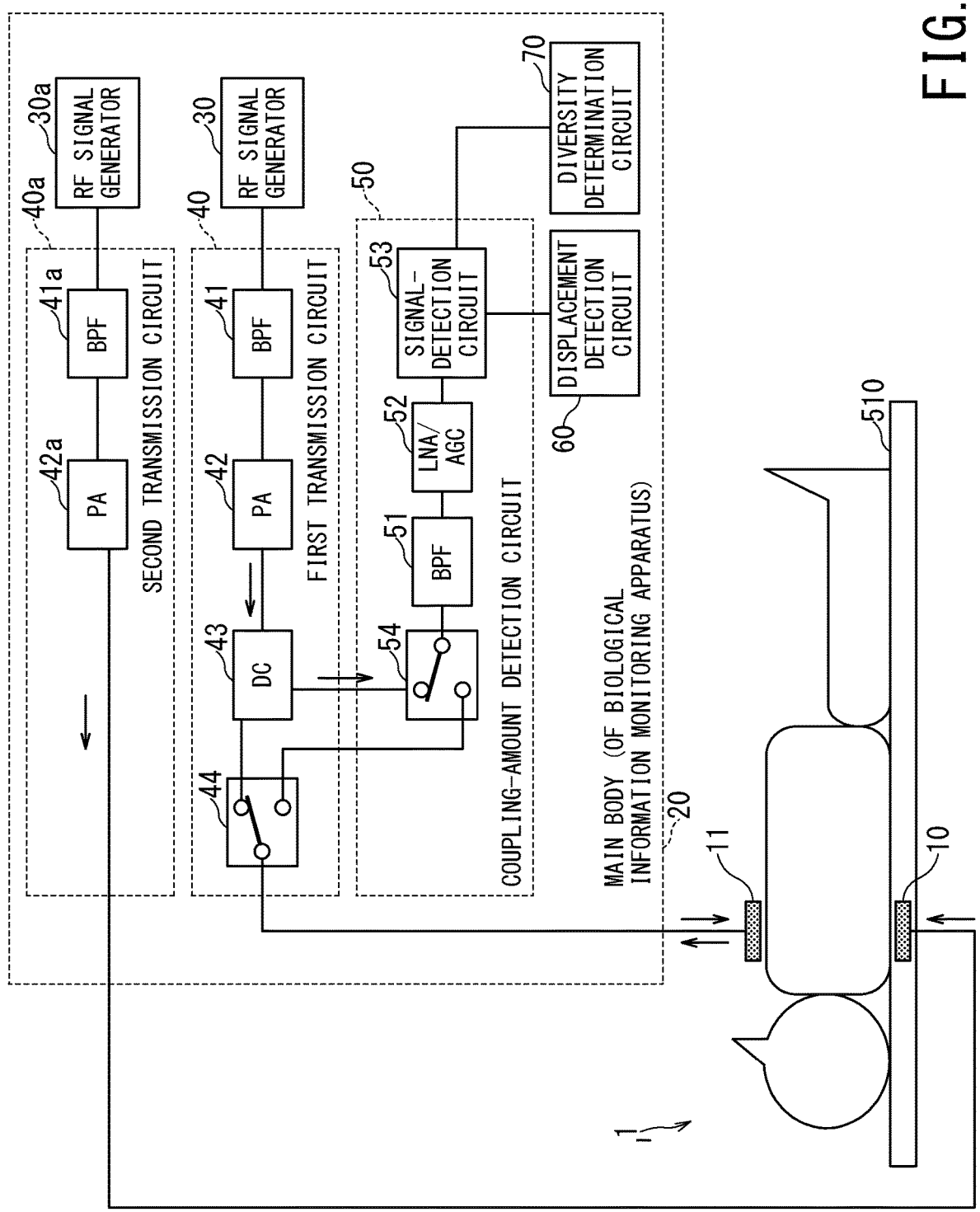
FIG. 10 is a block diagram illustrating an overall configuration of the biological information monitoring apparatus according to the third embodiment.

FIG. 10 is a configuration diagram illustrating an overall configuration of the biological information monitoring apparatus 1 according to the third embodiment. The biological information monitoring apparatus 1 of the third embodiment is a combination of the first embodiment and the second embodiment. Specifically, the third embodiment is configured to be able to select either one of the first mode corresponding to the first embodiment and the second mode corresponding to the second embodiment.

In the first mode, a high-frequency signal is inputted to the antenna 11, and the motion of the object such as heartbeat and/or respiration is measured on the basis of the reflected signal from the antenna 11, or on the basis of the S11 parameter of the antenna 11. In the second mode, a high-frequency signal is inputted to the antenna 10, and the motion of the object such as heartbeat and/or respiration is measured on the basis of the transmitted signal from the antenna 10 to the antenna 11, or on the basis of the S21 parameter from the antenna 10 to the antenna 11.

The RF signal generator 30 and the first transmission circuit 40 are configurations corresponding to the function for generating a high-frequency signal in the first mode. On the other hand, the RF signal generator 30a and the second transmission circuit 40a are configurations corresponding to the function for generating a high-frequency signal in the second mode. The coupling-amount detection circuit 50 is used in common in both of the first mode and the second mode.

The diversity determination circuit 70 monitors the reflected signal detected in the first mode and the transmitted signal detected in the second mode, and selects either one of the first mode and the second mode. When monitoring the reflected signal in the first mode, the diversity determination circuit 70 switches both of the switch 44 of the first transmission circuit 40 and the switch 54 of the coupling-amount detection circuit 50 to the side of the directional coupler 43 as shown in the state of FIG. 10. When monitoring the transmitted signal in the second mode, the diversity determination circuit 70 switches the switches 44 and 54 to the opposite sides in a state shown in FIG. 10.

The diversity determination circuit 70 compares the fluctuation range (i.e., amplitude of fluctuations) of the reflected signal in the first mode with the fluctuation range of the transmitted signal in the second mode, and selects the mode having the larger fluctuation range. For example, when it is determined that the monitored fluctuation range of the reflected signal is larger than the monitored fluctuation range of the transmitted signal, the diversity determination circuit 70 selects the first mode. Alternatively, the diversity determination circuit 70 may individually perform Fourier transform on the reflected signal and the transmitted signal, and then may select the mode in which the frequency component corresponding to the heartbeat is larger, or may select the mode in which the frequency component corresponding to the respiration is larger.

After selecting either one of the first mode and the second mode, the diversity determination circuit 70 sets and fixes the switches 44 and 54 to the state corresponding to the selected mode, then measures either one of the reflected signal and transmitted signal under the selected mode, and then detects the body motion signal such as heartbeat and a respiratory motion.

Modification of Third Embodiment

The biological information monitoring apparatus 1 of the modification of the third embodiment performs diversity processing by using two or more antennas 10 and 11. In this diversity processing, one antenna that detects the body motion signal with maximum sensitivity is selected or a combination of two or more antennas that can detect the body motion signal with maximum sensitivity is selected.

Figure 11A:
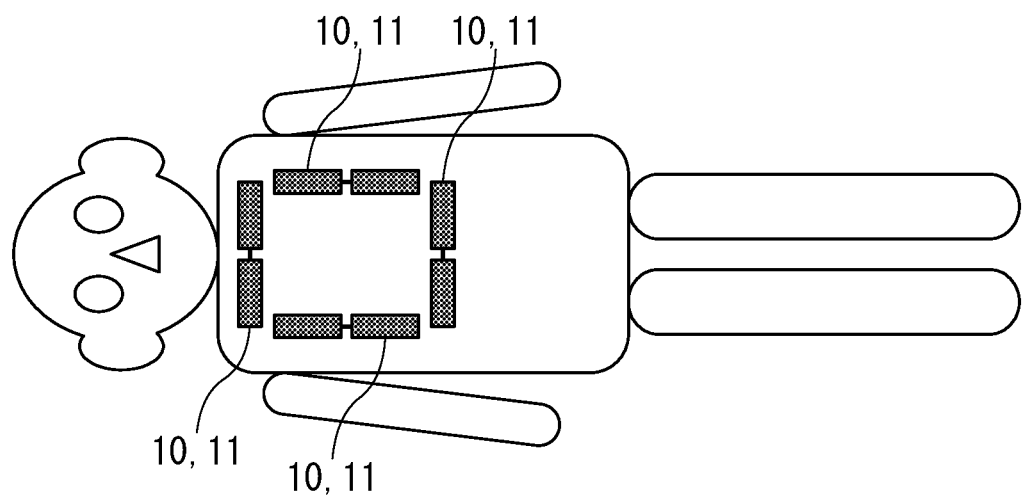
FIG. 11A and FIG. 11B are schematic diagrams illustrating disposition of four antennas for performing diversity processing.
Figure 11B:
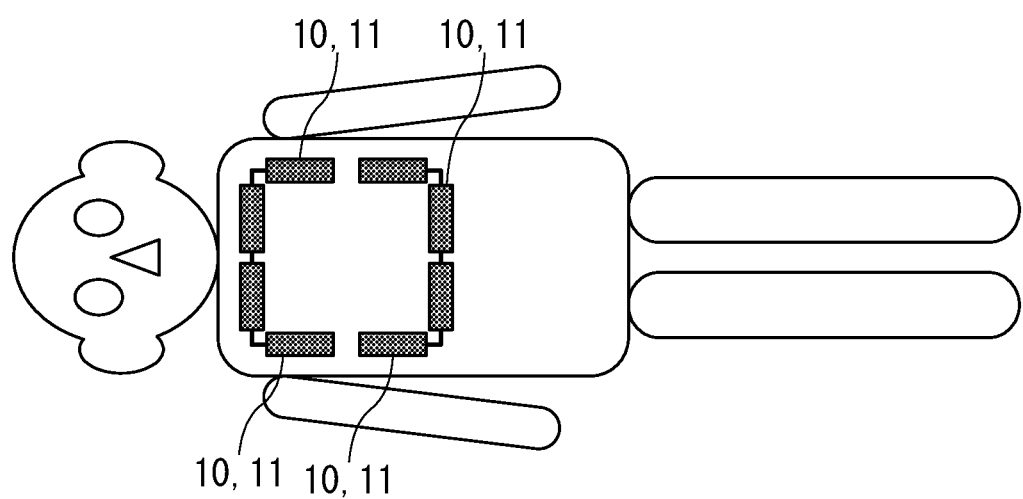

FIG. 11A and FIG. 11B are schematic diagrams illustrating disposition of four antennas for performing the diversity processing. In this case, for example, as shown in FIG. 11A, four dipole antennas 10 and 11 may be disposed so as to surround the heart. Further, as shown in FIG. 11B, the antennas 10 and 11, in each of which the dipole antenna is bent at a substantially right angle at the center, may be disposed so as to surround the heart.

In the case of performing the diversity processing by using the biological information monitoring apparatus 1 of the first embodiment, or in the case of performing the diversity processing in the first mode of the third embodiment, one antenna that can detect the body motion signal with maximum sensitivity is selected among the four antennas.

Alternatively, in the case of performing the diversity processing by using the biological information monitoring apparatus 1 of the second embodiment, or in the case of performing the diversity processing in the second mode of the third embodiment, for example, one antenna is selected as a transmission antenna 10, and further, one antenna capable of detecting the body motion signal with maximum sensitivity is selected among the remaining three antennas as a reception antennas 11, or synthetic antenna processing is performed by using an arbitrary combination of the remaining three antennas, causing a synthesized reception antenna 11.

In the modification of the third embodiment, for example, a circuit having a function similar to that of the diversity determination circuit 70 shown in FIG. 10 may be provided so that this circuit performs the above-described antenna-selection processing and/or synthetic antenna processing.

(MRI Apparatus)

Figure 12:
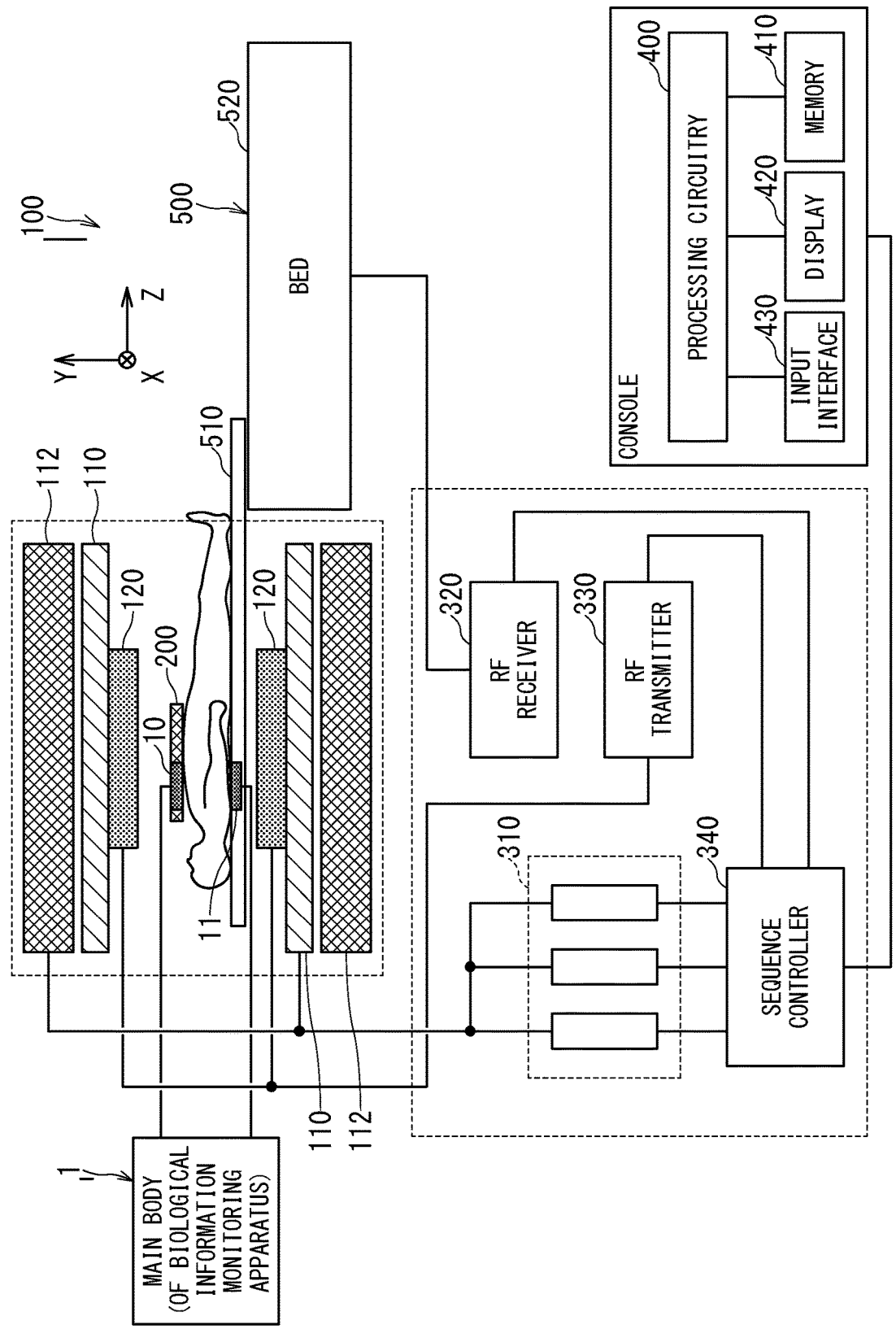
FIG. 12 is a configuration diagram illustrating an MRI apparatus that is provided with the biological information monitoring apparatus of one of the embodiments.

FIG. 12 is a configuration diagram illustrating an MRI apparatus 100 that is provided with the biological information monitoring apparatus 1 according each embodiment described above.

The MRI apparatus 100 includes a static magnetic field magnet 112, a gradient coil 110, and a whole body (WB) coil 120, and these components are housed in a cylindrical housing. The MRI apparatus 100 also includes: a bed 500 provided with a bed body 520 and a table 510; and at least one RF coil 200 disposed close to the object. The RF coil 200 is also referred to as a local coil or surface coil.

The MRI apparatus 100 further includes a gradient coil power supply 310, an RF receiver 320, an RF transmitter 330, and a sequence controller 340. The MRI apparatus 100 further includes a console, i.e., a computer that is provided with processing circuitry 400, a memory 410, a display 420, and an input interface 430.

The biological information monitoring apparatus 1 includes the antennas 10 and 11 in addition to the main body 20 shown in FIG. 1, FIG. 6, and FIG. 10. The antennas 10 and 11 are disposed close to the object but are not required to be directly attached to the skin of the object. Although the antennas 10 and 11 may be individually disposed in the vicinity of the object, the antennas 10 and 11 may be embedded in the RF coil 200 as shown in FIG. 12 or may be embedded in the table 510.

FIG. 13A is a block diagram illustrating a configuration of the biological information monitoring apparatus 1, which is used in the MRI apparatus 100. Although the MRI apparatus 100 can be used along with any of the above-described embodiments, FIG. 13A illustrates the biological information monitoring apparatus 1 of the second embodiment.

The MRI apparatus 100 can prospectively acquire MR signals based on the physical displacement of the object detected by the biological information monitoring apparatus 1. For example, a synchronization signal corresponding to an R wave can be generated from the heartbeat signal detected by the biological information monitoring apparatus 1, and the MR signals can be prospectively acquired using the synchronization signal.

Further, the MRI apparatus 100 may retrospectively reconstruct the MR signals acquired by the MRI apparatus 100 based on the physical displacement of the object detected by the biological information monitoring apparatus 1.

In the MRI apparatus 100, the RF transmitter 330 outputs an RF pulse for causing magnetic resonance with very high power, and the RF pulse is emitted from the WB coil 120 toward the object. With this emission, very large RF power is inputted to the main body 20 of the biological information monitoring apparatus 1 via the antennas 10 and 11.

Thus, in the biological information monitoring apparatus 1 used in the MRI apparatus 100, the protection switches 45 and 55 are respectively provided at the output terminal of the transmission circuit 40 and the input terminal of the coupling-amount detection circuit 50. The protection switches 45 and 55 are turned on and off by using a control signal sent from the main body of the MRI apparatus 100.

FIG. 13B is a schematic diagram illustrating a transmission/reception period of a high-frequency signal for biological monitoring. As shown in FIG. 13B, in order to avoid interference between the MRI apparatus 100 and the biological information monitoring apparatus 1, the high-frequency signal for biological monitoring is transmitted and received during a period excluding the transmission period of each RF pulse for causing magnetic resonance and the reception period of each MR signal.

The repetition period T of the transmission/reception period of the high-frequency signal for biological monitoring can be defined from the period of heartbeat and/or the period of respiration. The frequency of heartbeat can be assumed to be approximately 2 Hz or less, and the frequency of respiration can be assumed to be approximately 0.5 Hz or less. From the view point of the sampling theorem, when sampling is performed at twice the higher frequency, i.e., at a frequency of 4 Hz or higher, the waveform of the heartbeat and the waveform of the respiration can be accurately extracted. Thus, the repetition period T may be set to 250 ms (=1/(4 Hz)) or less.

It is preferred that the frequency of the high-frequency signal for biological monitoring is higher than the Larmor frequency used for the MRI apparatus 100. When the frequency of the high-frequency signal for biological monitoring is set to be higher than the Larmor frequency, not only the high frequency signal itself for biological monitoring but also its harmonics can be prevented from entering the reception band of MR signal of the MRI apparatus 100.

Figure 14A:
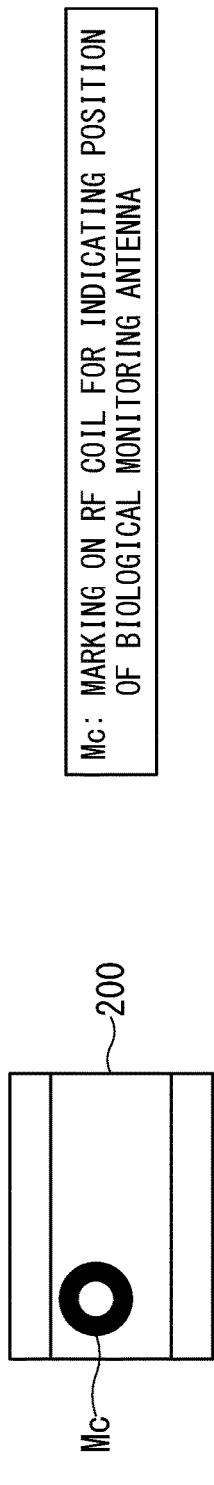
FIG. 14A is a schematic diagram illustrating marking that is performed on the RF coil to indicate the position of the antenna.
Figure 14B:
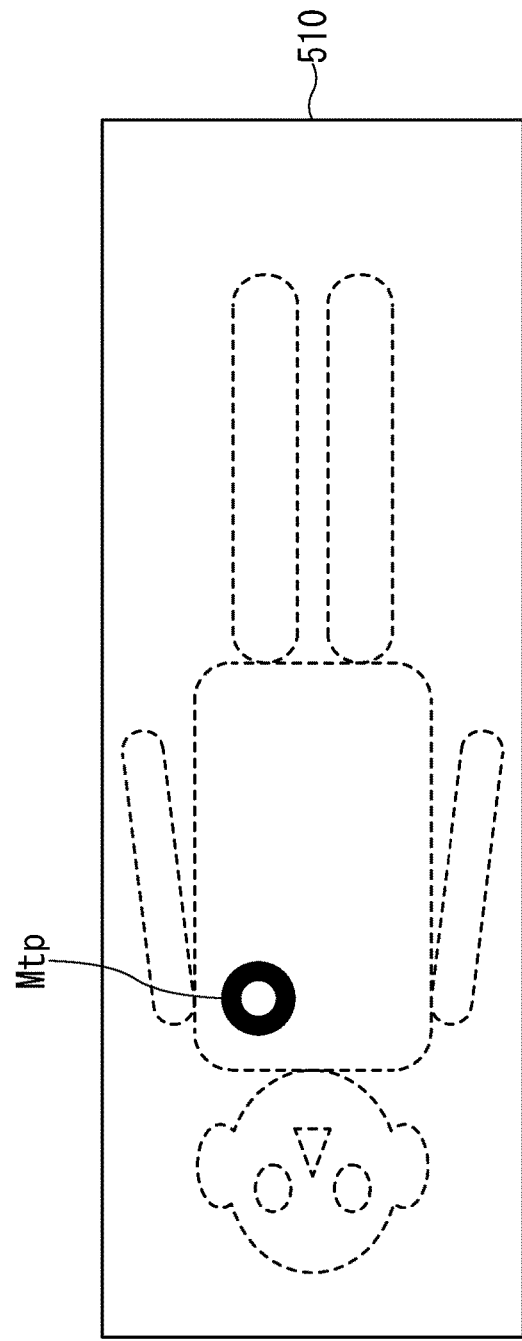
FIG. 14B is a schematic diagram illustrating marking that is performed on the table to indicate the position of the antenna.

FIG. 14A is a schematic diagram illustrating marking that is performed on the RF coil 200 to indicate the position of the antennas 10 and 11, and FIG. 14B is a schematic diagram illustrating marking that is performed on the table 510 to indicate the position of the antennas 10 and 11. As described above, the antennas 10 and 11 of the biological information monitoring apparatus 1 can be mounted by being embedded in the RF coil 200 or the table 510 of the bed 500. In the case of measuring heartbeat, it is preferred that the antennas 10 and 11 are disposed near the heart of the object. Thus, marking is preferably provided such that a user can readily and visually recognize the antennas 10 and 11 embedded in the RF coil 200 and/or table 510, and further, the respective positions of the object and the RF coil 200 are preferably adjusted such that this marking is near the heart of the object.

(Embodiment of Antenna with Parasitic Element)

So far, as shown in FIG. 5A to FIG. 5D, FIG. 9A to FIG. 9D, FIG. 11A, and FIG. 11B, the dipole antenna, particularly the half-wave dipole antenna, has been described as an embodiment of the antenna 10 (or antenna 11) to be used in the biological information monitoring apparatus 1.

However, a conventional dipole antenna has a single resonance and exhibits narrow band characteristics as described below, and thus, has been found to cause the following problem in some cases. That is, when such a conventional antenna is used in the above-describe biological information monitoring apparatus 1, in some cases, the antenna characteristics greatly fluctuate due to the influence of body motions such as a respiratory motion of the abdomen and the heartbeat waveform to be detected is disturbed, which makes it difficult to detect the heartbeat waveform.

Regarding above-described problem, the bandwidth of the antenna used for the biological information monitoring apparatus 1 can be widened by an antenna with a parasitic element, and it has also been found that such a band-widened antenna can solve the above-described problem.

Hereinafter, various embodiments of the antenna with a parasitic element will be described by referring to FIG. 15A to FIG. 28C. In the following, the antenna with a parasitic element is denoted as the transmission antenna 10 for detecting the S11 parameter, but the antenna with a parasitic element can also be used for both of the transmission antenna 10 and the reception antenna 11 for detecting the S21 parameter.

Figure 15A:
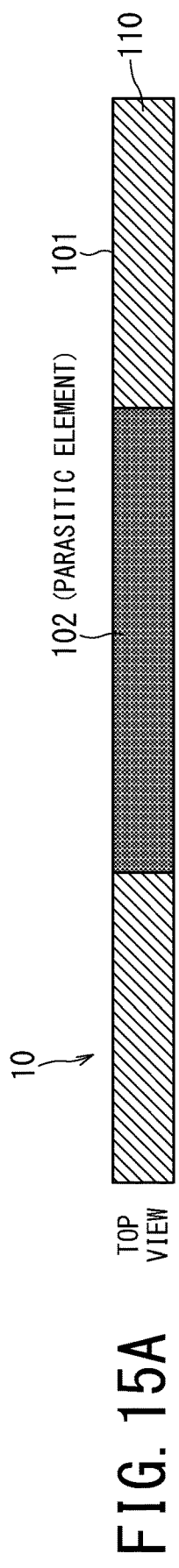
FIG. 15A to FIG. 15C are schematic diagrams illustrating an appearance and a configuration of the antenna according to the first embodiment of an antenna with a parasitic element.
Figure 15B:
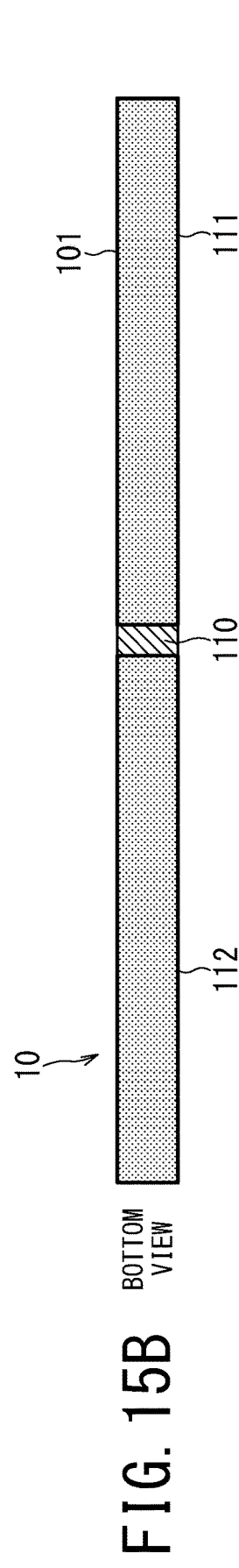
Figure 15C:
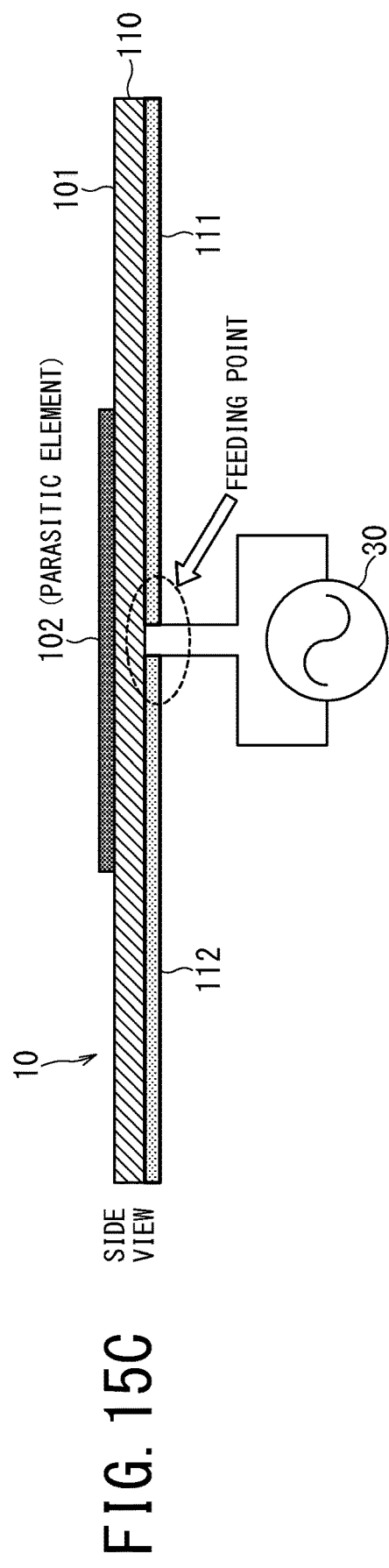

FIG. 15A to FIG. 15C are schematic diagrams illustrating an appearance and a configuration of the antenna 10 according to the first embodiment of the antenna with a parasitic element. FIG. 15A is a top view (or front view) of the antenna 10, FIG. 15B is a bottom view (or back view) of the antenna 10, and FIG. 15C is a side view of the antenna 10. Here, the top face of the antenna 10 is the face far from the object when the antenna 10 is placed on the object, and the bottom face is the face closer to the object (i.e., the side in contact with the object).

The antenna 10 includes a main antenna 101 and a parasitic element 102. The main antenna 101 is, for example, a planar dipole antenna. The parasitic element 102 is a conductor placed near the feeding point of the main antenna 101.

As shown in FIG. 15C, on the bottom side of the substrate 110 of the main antenna 101, a feeding point and two rectangular planar conductors 111 and 112 are formed such that the feeding point is interposed between the planar conductor 111 positioned on one side (for example, right side) of the feeding point and the planar conductor 112 positioned on the opposite side (for example, left side) of the feeding point. The substrate 110 is, for example, an insulating resin substrate, and the planar conductors 111 and 112 are, for example, copper foils formed on the resin substrate. The high-frequency signal generated by the RF signal generator 30 is supplied to the feeding point provided in the center of the main antenna 101.

The parasitic element 102 is disposed on the face of the main antenna 101 opposite to the planar conductors 111 and 112, for example, on the top side such that the substrate 110 is interposed between the parasitic element 102 and the planar conductors 111 and 112. The parasitic element 102 is also a rectangular planar conductor, and is formed of, for example, a copper plate or a copper foil.

A high frequency signal is fed to the main antenna 101, whereas a high frequency signal is not fed to the parasitic element 102. Further, the parasitic element 102 is arranged so as to be superimposed with a feeding point and a part of the region of the main antenna 101.

While the parasitic element 102 is not connected to the main antenna 101, it affects the operation of the main antenna as shown below.

Figure 16B:
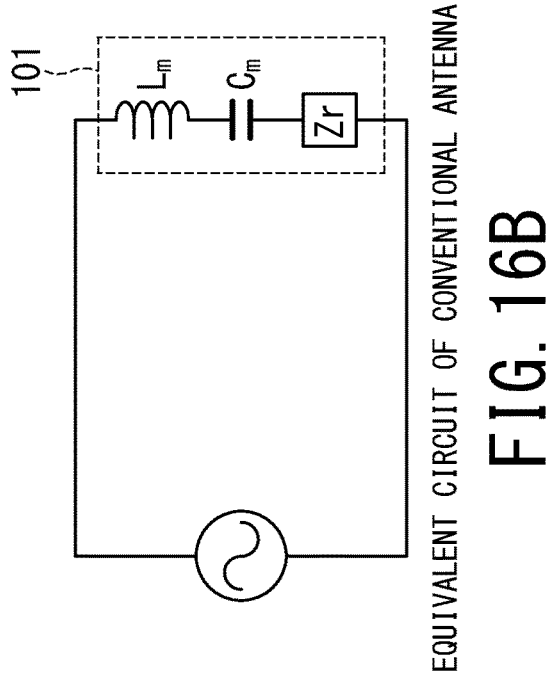
FIG. 16A and FIG. 16B illustrate a conventional antenna without a parasitic element and its equivalent circuit.

The parasitic element 102 is capacitively coupled with the main antenna 101, and thereby, these components are equivalent to a configuration in which a capacitor and an inductor are connected in parallel with respect to the main antenna 101. FIG. 16A and FIG. 16B show a conventional antenna without a parasitic element 102 and its equivalent circuit, respectively. The equivalent circuit of the conventional antenna is a series resonant circuit in which an inductor Lm, a capacitor Cm, and a radiation resistor Zr are connected in series. Thus, the frequency characteristic of the conventional antenna shows a single resonance characteristic defined by the inductor Lm and the capacitor Cm.

Figure 16D:
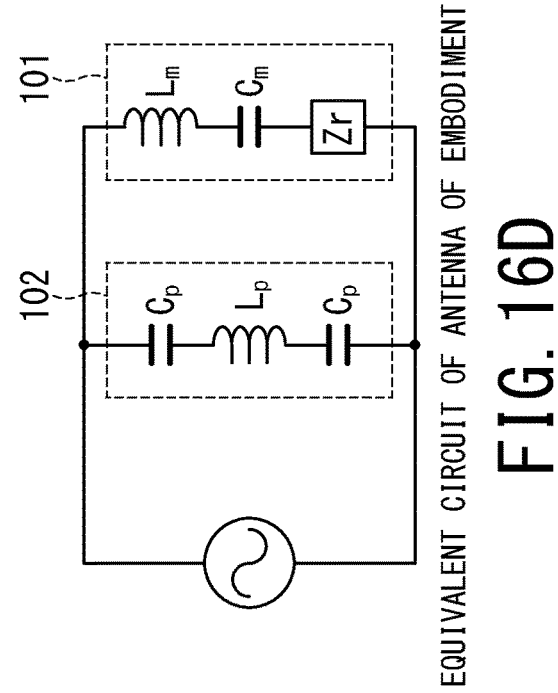
FIG. 16C and FIG. 16D illustrate the antenna with the parasitic element of the present embodiment and its equivalent circuit.
Figure 16A:
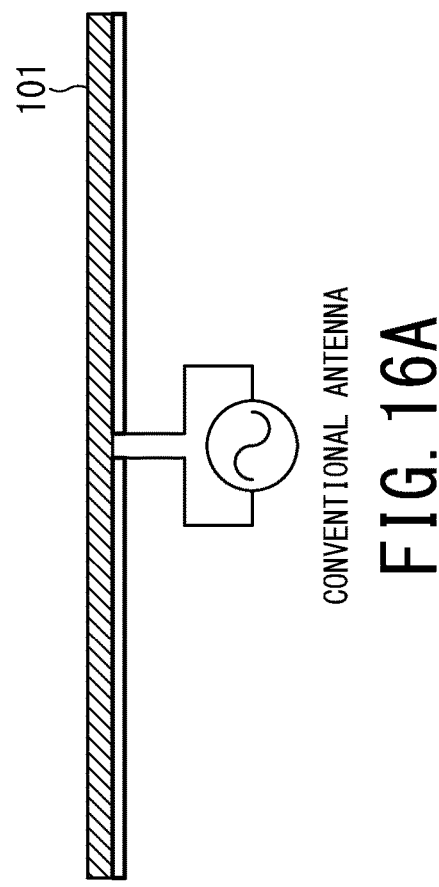
Figure 16C:
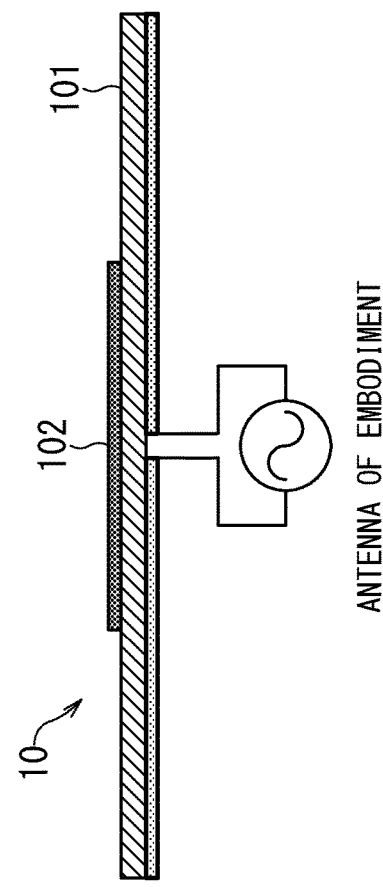

FIG. 16C and FIG. 16D illustrate the antenna 10 with the parasitic element 102 of the present embodiment and its equivalent circuit, respectively. The main antenna 101 of the antenna 10 is substantially the same as the conventional antenna shown in FIG. 16A. Thus, the equivalent circuit of the main antenna 101 is a series resonant circuit in which the inductor Lm, the capacitor Cm, and the radiation resistor Zr are connected in series. As described above, the parasitic element 102 is capacitively coupled with the main antenna 101, and consequently, the equivalent circuit of the antenna 10 of the present embodiment becomes a circuit in which the series circuit of the capacitor Cp and the inductor Lp is connected in parallel to the main antenna 101. The capacitance of the capacitor Cp is mainly defined by the size of the gap between the parasitic element 102 and the main antenna 101 and the overlapping area between the parasitic element 102 and the main antenna 101. The inductance of the inductor Lp is mainly defined by the length of the parasitic element 102.

Since the parasitic element 102 is added in the antenna 10 of the present embodiment, the series resonant circuit including the capacitor Cp and the inductor Lp of the parasitic element 102 is formed in addition to the series resonant circuit including the inductor Lm and the capacitor Cm of the main antenna 101, and further, these two series resonance circuits are connected in parallel so as to cause parallel resonance. As a result, the antenna 10 of the present embodiment can realize the multiple resonance characteristic and can have a wider bandwidth than the conventional antenna.

Figure 17B:
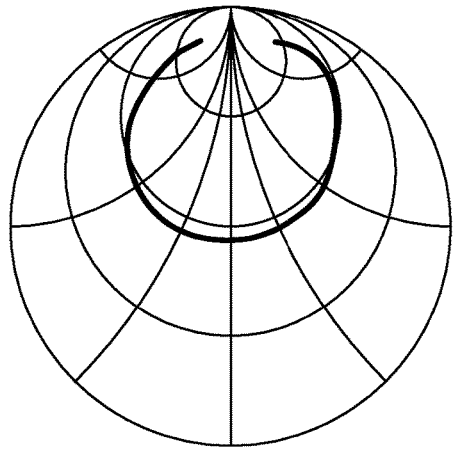
FIG. 17A and FIG. 17B are schematic diagrams in which the frequency characteristics of the S11 parameter of the conventional antenna are plotted as a locus on the Smith chart.
Figure 17D:
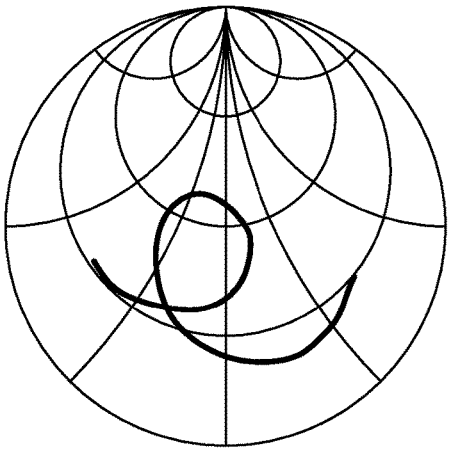
FIG. 17C and FIG. 17D are schematic diagrams in which the frequency characteristics of the S11 parameter of the antenna of the present embodiment are plotted as a locus on the Smith chart.
Figure 17A:
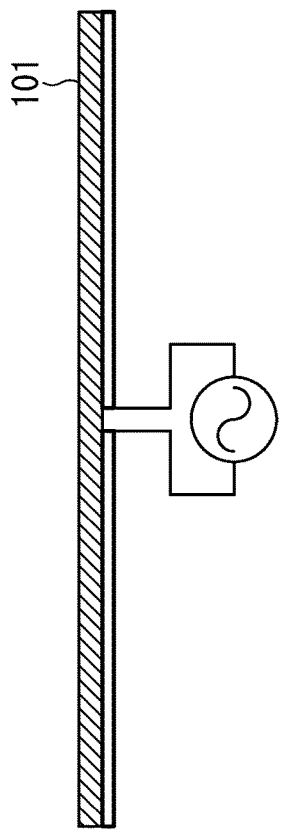
Figure 17C:
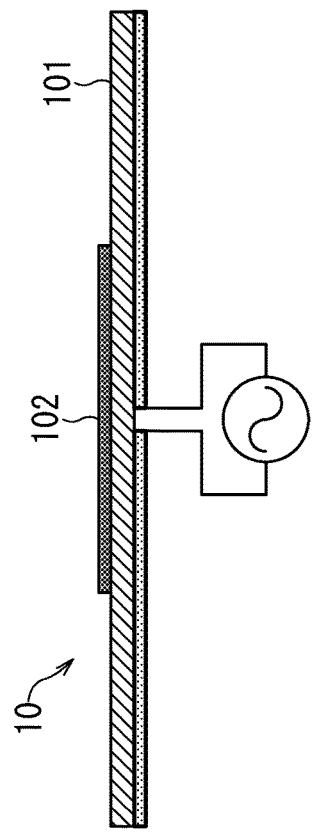
Figure 18B:
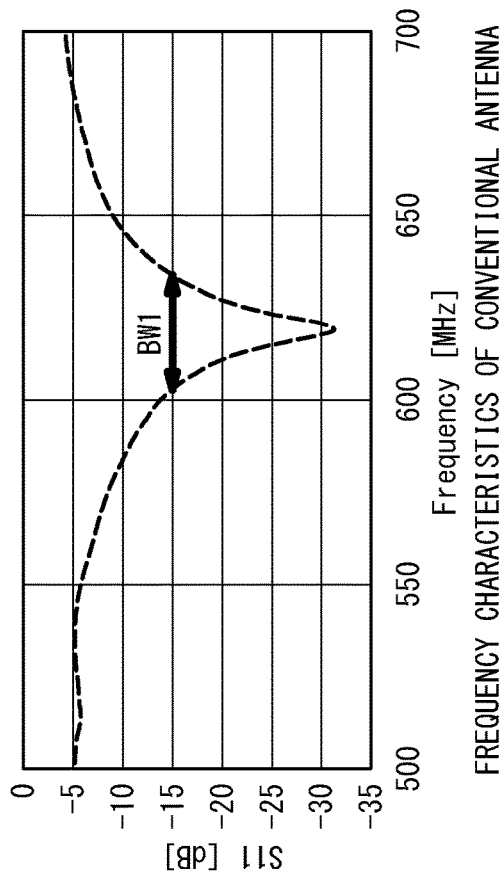
FIG. 18A to FIG. 18D are schematic diagrams illustrating a comparison of measurement results of the frequency characteristics of the S11 parameter between the conventional antenna and the antenna of the present embodiment.
Figure 18D:
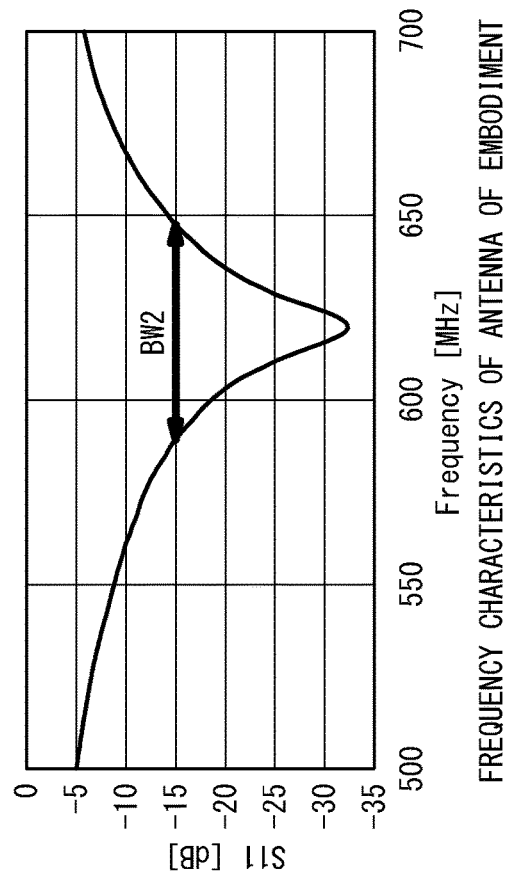
Figure 18A:
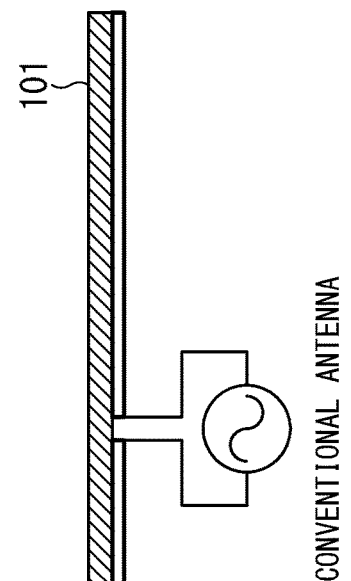
Figure 18C:
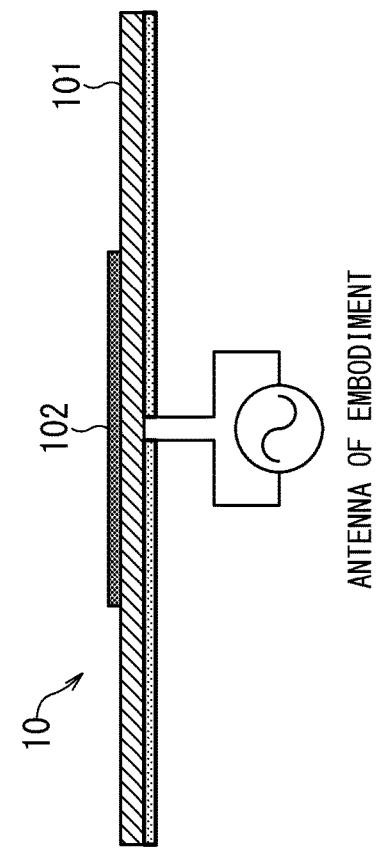

FIG. 17D illustrates the frequency characteristics of the complex reflection coefficient (or S11 parameter) of the antenna 10 of the present embodiment such that the complex reflection coefficient is plotted as a locus on the Smith chart. On the Smith chart, the frequency at which the locus crosses the real axis (i.e., horizontal axis passing through the center of the circle) is the resonance frequency. This is because crossing the real axis means that the reactance component becomes zero. The Smith chart of the conventional antenna shown in FIG. 17B shows the characteristic that the locus moves on a relatively large circle, and the locus crosses the real axis only once at one point near the center of the circle. This means that the conventional antenna has only one resonance frequency and has a single resonance characteristic.

By contrast, the locus of the antenna 10 of the embodiment shown in FIG. 17D has a loop shape surrounding the center of the Smith chart, and the locus crosses the real axis a plurality of times. In particular, the locus crosses the real axis twice near the center of the Smith chart. This means that the antenna 10 of the embodiment has a plurality of (at least two) different resonance frequencies and has multiple resonance characteristics.

From the locus on the Smith chart, it can be understood that the antenna 10 of the embodiment has a wider band characteristic than the conventional antenna.

FIG. 18A to FIG. 18D are schematic diagrams illustrating a comparison of measurement results of the frequency characteristics of the S11 parameter (decibel value) between the conventional antenna and the antenna 10 of the embodiment. Based on the magnitude relation (BW2>BW1) between the bandwidths BW1 and BW2 at the same S11 parameter value (for example, −15 dB), it is obvious that the antenna 10 of the embodiment has a wider bandwidth than the conventional antenna. That is, the antenna 10 of the embodiment can obtain S11 parameters smaller than a predetermined value over a wider frequency range.

When the antenna 10 having the above-described wideband characteristics is used for the biological information monitoring apparatus 1, the frequency shift of the characteristics of the S11 parameter due to respiratory motions of a human body is reduced as compared with the conventional antenna. This fact is also supported by the measurement results of the frequency characteristics of the S11 parameter under respiration.

Figure 19B:
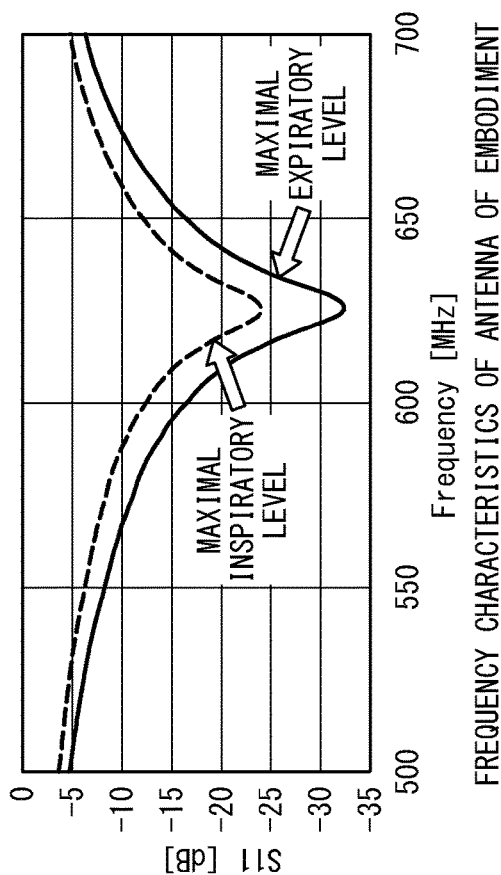
FIG. 19A to FIG. 19D are schematic diagrams illustrating a comparison of the frequency characteristics of the S11 parameter measured at the maximal inspiratory level and the maximal expiratory level between the conventional antenna and the antenna of the present embodiment.

FIG. 19A to FIG. 19D are schematic diagrams illustrating a comparison of the frequency characteristics of the S11 parameter measured at the maximal inspiratory level and the maximal expiratory level between the conventional antenna and the antenna 10 of the embodiment. FIG. 19B illustrates the measurement results of the conventional antenna. At the maximal inspiratory level and the maximal expiratory level, a considerable frequency shift occurs in the characteristics of the S11 parameter of the conventional antenna.

Figure 19D:
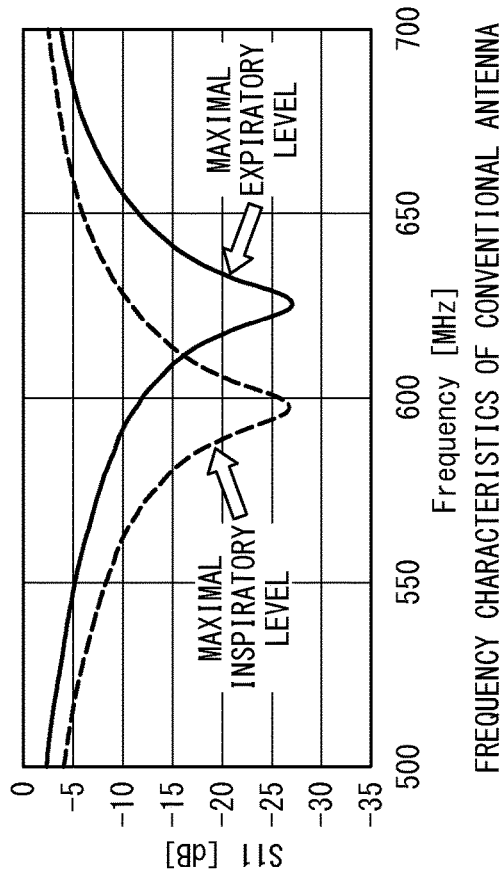
Figure 19A:
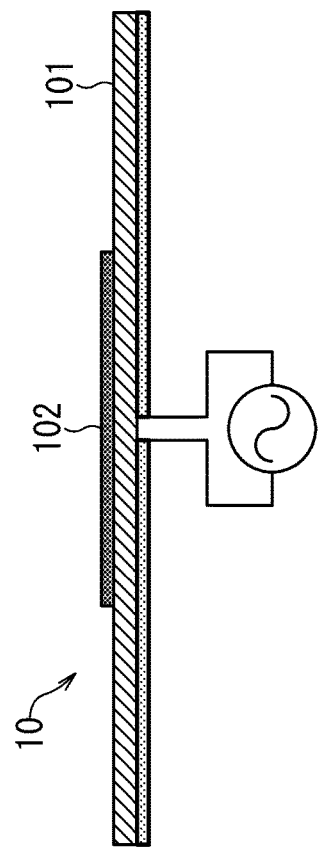
Figure 19C:
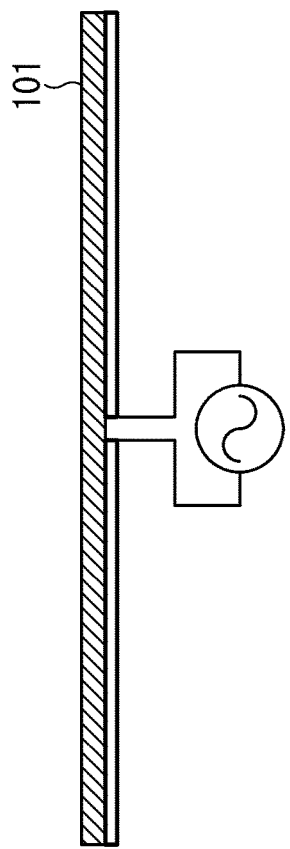

FIG. 19D illustrates the measurement result of the antenna 10 of the present embodiment. At the maximal inspiratory level and the maximal expiratory level, the frequency characteristics of the S11 parameter shift in the vertical axis direction (i.e., in the magnitude direction of the S11 parameter) but hardly shift in the frequency direction. It can be considered that the addition of the parasitic element 102 causes parallel resonance that widens the bandwidth and leads to reduction in frequency shift of the frequency characteristic of the S11 parameter.

FIG. 20A to FIG. 20D are schematic diagrams illustrating a comparison of the result of measuring the frequency shift of the frequency characteristic of the S11 parameter in association with the locus on the Smith chart between the conventional antenna and the antenna 10 of the embodiment.

Figure 20B:
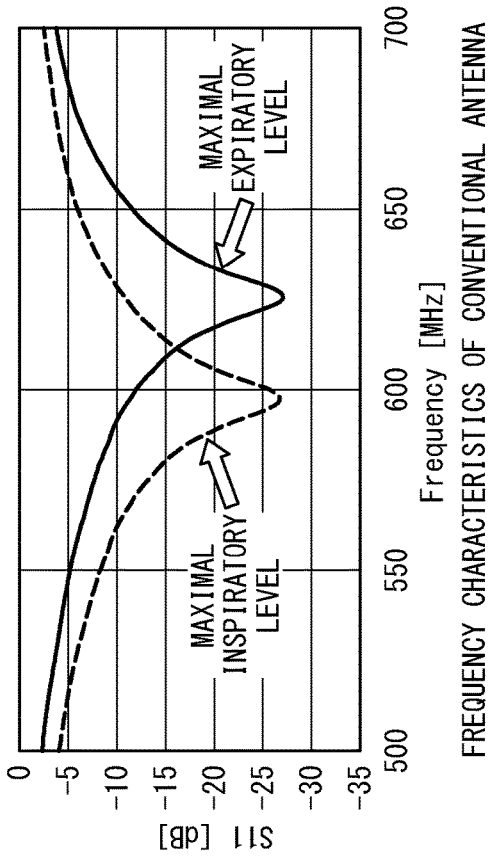
FIG. 20A to FIG. 20D are schematic diagrams illustrating a comparison of measured frequency shift of the frequency characteristic of the S11 parameter in association with the locus on the Smith chart between the conventional antenna and the antenna of the present embodiment.
Figure 20D:
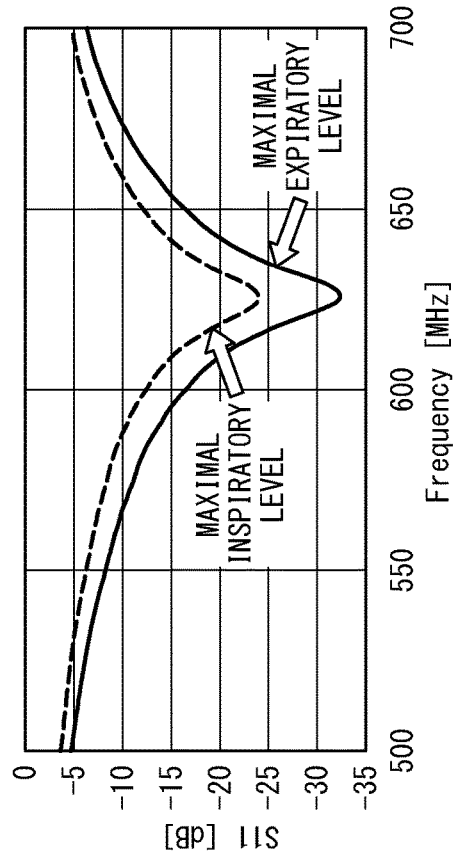
Figure 20A:
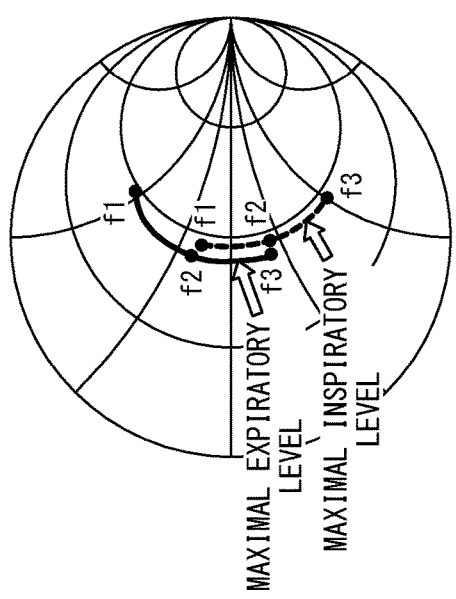

As described above, the conventional antenna without the parasitic element 102 shows the characteristic that the locus moves on a relatively large circle on the Smith chart, and the locus crosses the real axis only once at one point near the center of the circle. When measurement is performed under respiration, as shown in FIG. 20A, the locus on the Smith chart (for example, from frequencies f1 to f2 and from f2 to f3) shows the movements in circular arc shapes which are considerably far apart between the maximum expiratory level and the maximum inspiratory level. The absolute value of the S11 parameter is expressed as the distance from the center position of the Smith chart. The frequency at which the absolute value of the S11 parameter is minimized is the frequency at which the distance from the center position of the Smith chart is the shortest. In the case of FIG. 20A, at the maximum expiratory level, the frequency between f2 and f3 is closest to the center position, and thus, the S11 parameter is minimized at the frequency between f2 and f3. On the other hand, at the maximal inspiratory level, the frequency between f1 and f2 is closest to the center position, and the S11 parameter is minimized at the frequency between f1 and f2. That is, the frequency at which the S11 parameter is minimized differs between the maximum expiratory level and the maximum inspiratory level, and the locus on the Smith chart also indicates that the frequency shift of the S11 parameter characteristic occurs due to respiratory body motions.

Figure 20C:
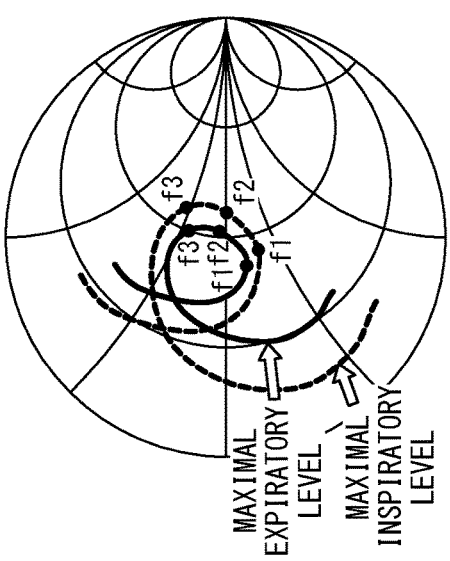

Meanwhile, FIG. 20C is a schematic diagram illustrating a locus on the Smith chart measured at the maximum expiratory level and the maximum inspiratory level by using the antenna 10 of the embodiment. As described above, the locus of the antenna 10 of the embodiment has a loop shape surrounding the center of the Smith chart. Although the size of the loop changes between the maximal expiratory level and the maximal inspiratory level, the frequency closest to the center position of the Smith chart (i.e., frequency at which the S11 parameter is minimized) is almost the same at the maximal expiratory level and the maximal inspiratory level. In the case shown in FIG. 20C, at both of the maximum expiratory level and the maximum inspiratory level, the frequency f2 is the frequency closest to the center position of the Smith chart, and the S11 parameter is minimized at the frequency f2. As described above, in the antenna 10 of the embodiment, it can be understood from the locus on the Smith chart that the frequency shift of the S11 parameter characteristic due to the respiratory body motion hardly occurs.

Figures 21A, 21B:
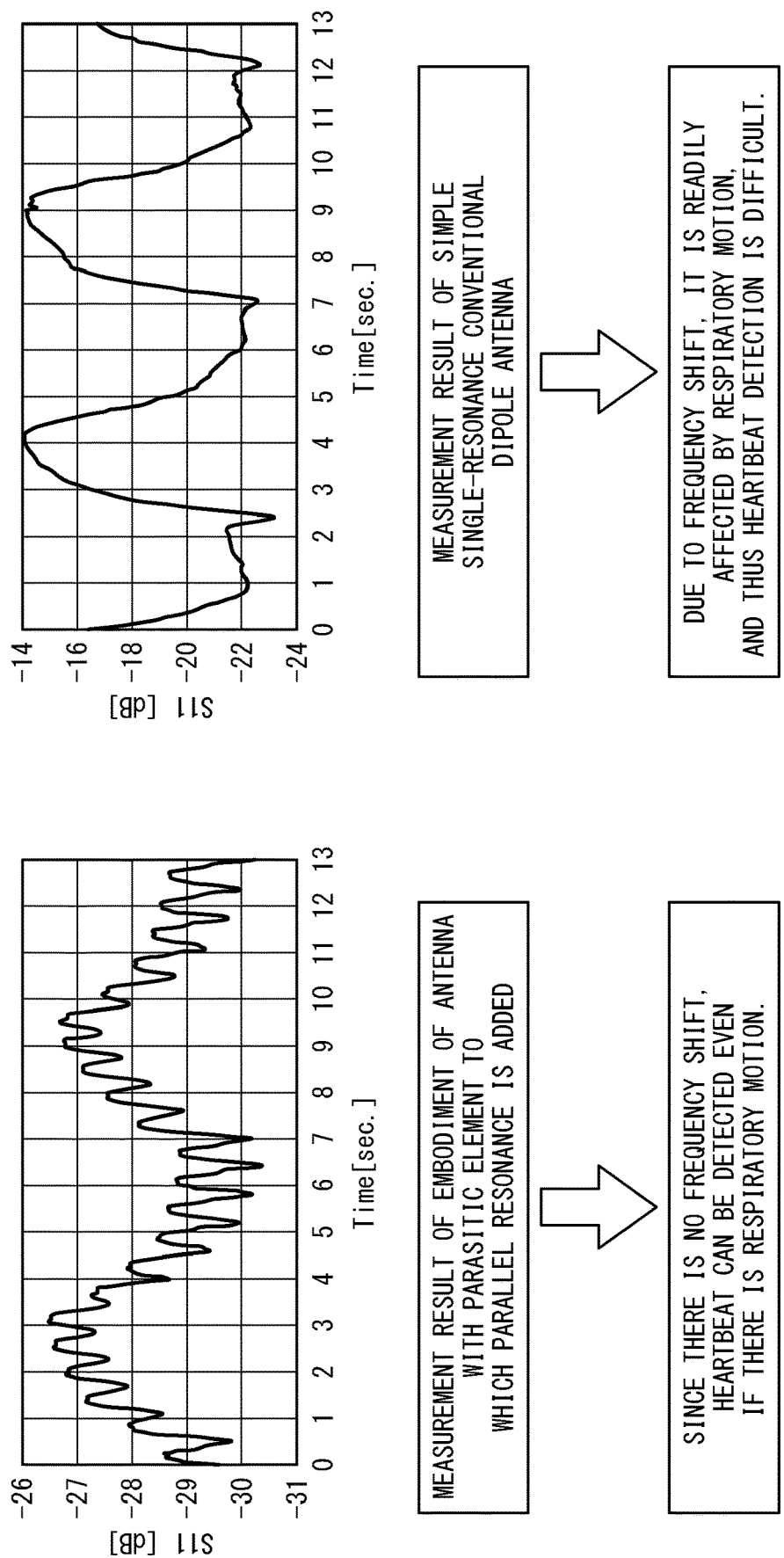
FIG. 21A and FIG. 21B are schematic diagrams illustrating the result of measuring time change of the S11 parameter.

FIG. 21A and FIG. 21B are schematic diagrams illustrating the result of measuring time change of the S11 parameter. FIG. 21A shows the result of measuring the time change of the S11 parameter by the biological information monitoring apparatus 1 using the antenna 10 of the embodiment. On the other hand, FIG. 21B shows the results of measuring the time change of the S11 parameter by the biological information monitoring apparatus 1 using the conventional antenna. In the graph of FIG. 21A, the short-cycle fluctuation is the S11 parameter fluctuation due to heartbeat and the long-cycle fluctuation is the S11 parameter fluctuation due to respiration. The short-cycle fluctuation due to the heartbeat superimposed on the gradual fluctuation of the respiratory motion is shown clearly, and the fluctuation due to the heartbeat as well as the fluctuation due to the respiratory motion can be easily detected from the graph of FIG. 21A. As described above, in the antenna 10 of the embodiment with the parasitic element 102, there is almost no frequency shift, and thus, the heartbeat can be detected even when respiratory motions are included.

On the other hand, in the measurement results using the conventional antenna shown in the graph of FIG. 21B, the long-cycle fluctuation due to the respiratory motion can be detected, but the short-cycle fluctuation due to heartbeat hardly appears. Since the conventional antenna has a frequency shift, the conventional antenna is susceptible to the respiratory motions and has a difficulty in detecting heartbeat in some cases.

Since the antenna 10 of the embodiment is provided with the parasitic element 102, the antenna 10 of the embodiment can generate not only series resonance but also parallel resonance, and thus, can realize a wide bandwidth. Further, the antenna 10 of the embodiment can reduce the frequency shift of the S11 parameter characteristic. Moreover, due to the widened bandwidth and reduction in frequency shift of the antenna 10 of the embodiment, the biological information monitoring apparatus 1 using the antenna 10 of the embodiment can prevent deterioration of heartbeat detection performance due to respiration, and can detect both of the heartbeat and the respiratory motions with high quality.

The above-described antenna 10 is installed close to the object when the heartbeat and/or the respiratory motion is detected and it is preferable to install the antenna 10 on the object in a manner that the parasitic element 102 being placed on the face farther from the object both faces of the main antenna 101 (for example, a planar dipole antenna) If the parasitic element 102 is placed on the face closer to the object, the effect of the parasitic element 102 is weakened because the capacitance coupling between the parasitic element 102 and the main antenna 101 is readily affected by the human body.

Note that, as an antenna that realizes a wide bandwidth, it is conceivable to use a multi-element wideband antenna in which a plurality of antenna elements having different resonance frequencies are combined. However, in multi-element wideband antennas, the physical size of the antenna increases as the number of elements increases. Contrastively, the antenna 10 of the embodiment to which the parasitic element 102 is added can obtain wideband characteristics without increasing the antenna size.

Antennas of Other Embodiments

Next, in addition to the antenna 10 of the first embodiment described above, the antenna 10 of some other embodiments will be described.

FIG. 22A is a top view illustrating an appearance and a configuration of the meander antenna 10 as the antenna 10 of the second embodiment, FIG. 22B is a bottom view of this meander antenna 10, and FIG. 22C is a side view of this meander antenna 10. The meander antenna 10 includes the main antenna 101 and the parasitic element 102 similarly to the antenna 10 of the first embodiment but differs in conductor pattern of the main antenna 101 from that of the first embodiment. In the main antenna 101 of the first embodiment, almost the entire bottom face of the planar dipole antenna is composed of a solid-pattern planar conductor 111 and a solid-pattern planar conductor 112. Here, the solid pattern (or the solid pattern surface) is a surface in which the entire substrate 110 is covered with a conductor layer without gaps, or a surface in which the entire substrate 110 is broadly and continuously covered with a conductor layer. Further, a region formed into the solid-pattern is a region in which the entire substrate 110 is covered with a conductor layer without gaps, or a region in which the entire substrate 110 is broadly and continuously covered with a conductor layer.

In the second embodiment, in both regions from the feeding point to the predetermined positions toward both ends of the dipole antenna element, the conductors on both sides of the planar dipole antenna are formed into a meander shape. Further, in the second embodiment, in both regions from the predetermined positions to both ends, the conductors on the bottom face of the planar dipole antenna are formed into a solid-pattern similarly to the first embodiment.

In the following description, a width direction is used as the direction that is orthogonal to both of the longitudinal direction (i.e., the direction of La in FIG. 23A) and the thickness direction of the substrate 110. The conductor region formed into the meander shape is a region of a pattern in which a thin conductor having a width sufficiently narrower than the width of the conductor in the width direction of the planar dipole antenna and is bent into a crank shape a plurality of times. In other words, the conductor region formed into the meander shape is the region of the pattern in which the conductor is formed as a so-called meander line.

Since part of the region in the longitudinal direction of the planar dipole antenna is formed by a meander-shaped conductor, the length in the longitudinal direction can be shortened and the antenna 10 can be downsized.

Further, the conductor of the planar dipole antenna is not entirely but partially made into a meander-shaped conductor, and the outer region of the antenna element excluding the meander region is formed as a solid-pattern of the conductor, which widens the bandwidth characteristics of the antenna.

FIG. 23A to FIG. 25C illustrate the antennas 10 of various embodiments for adjusting the frequency characteristics such as the bandwidth of the attenuation region and/or the magnitude of the attenuation on the frequency axis of the S11 parameter.

The antennas 10 of the various embodiments shown in FIG. 23A to FIG. 25C can be applied to both of the antenna 10 of the first embodiment shown in FIG. 15A to FIG. 15C and the meander antenna 10 of the second embodiment shown in FIG. 22A to FIG. 22C.

Figure 23A:
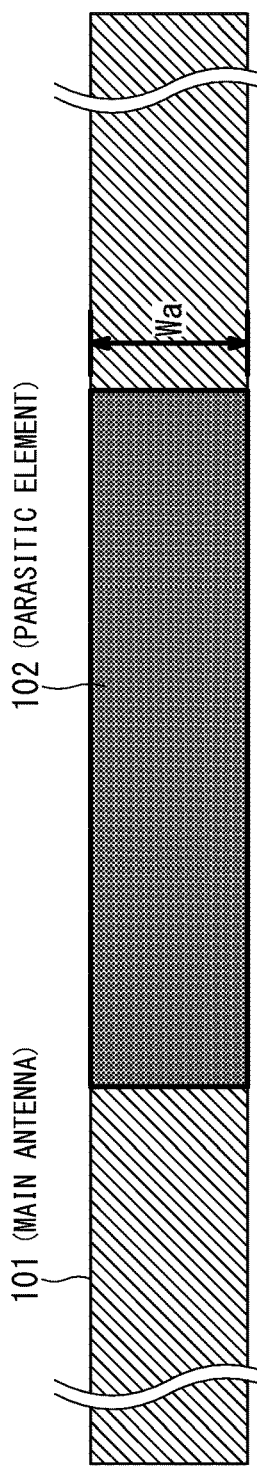
FIG. 23A to FIG. 23C are top views showing that the frequency characteristics of the antenna can be adjusted by changing the size of the parasitic element.
Figure 23B:
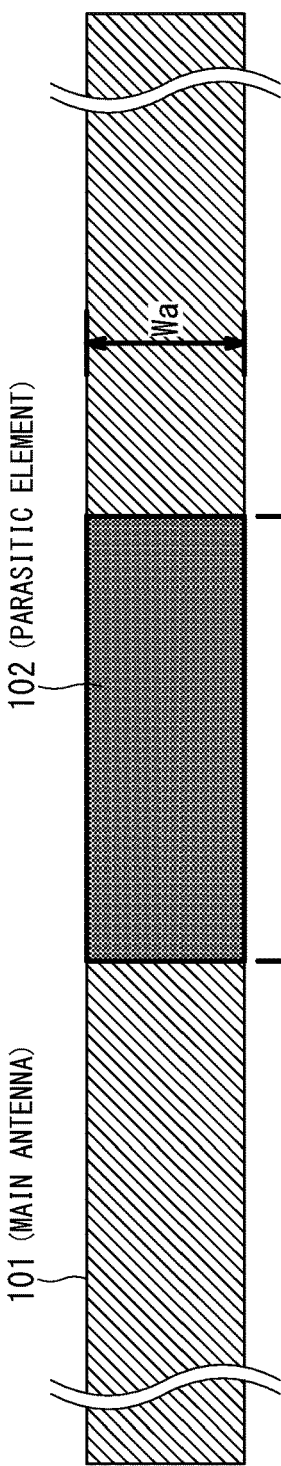
Figure 23C:
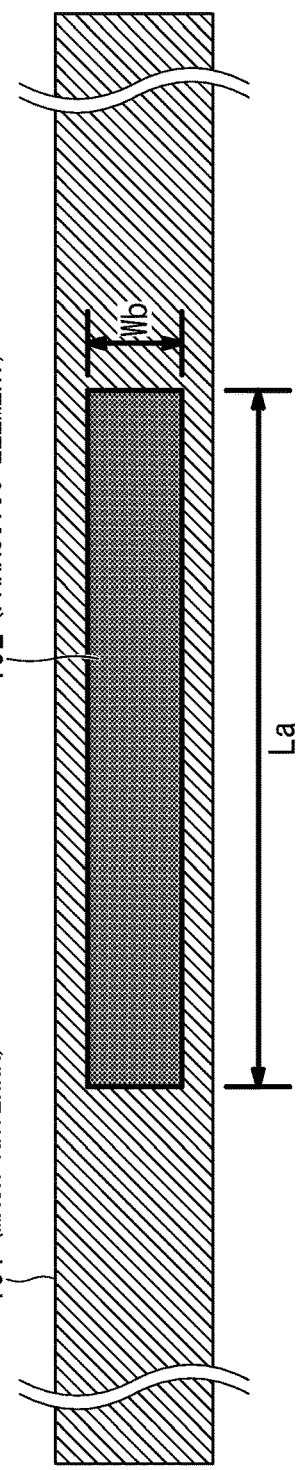

FIG. 23A to FIG. 23C are top views showing that the frequency characteristics of the antenna 10 can be adjusted by changing the size of the parasitic element 102. The main antenna 101 is configured as, for example, a planar dipole antenna having a meander-shaped conductor in the center of the antenna. The shape of the parasitic element 102 is configured as, for example, a square conductor having a predetermined length in the longitudinal direction of the planar dipole antenna and a predetermined width in the width direction of the planar dipole antenna.

In the antenna 10 having such a configuration as illustrated in FIG. 23A to FIG. 23C, the frequency characteristics of the antenna 10 can be adjusted by adjusting the width W of the parasitic element 102 to a different width such as Wa and Wb or by adjusting the length L of the parasitic element 102 to a different length such as La and Lb.

FIG. 24A, FIG. 24B, FIG. 25A, and FIG. 25B are schematic diagrams illustrating that the frequency characteristic of the antenna 10 can be adjusted by dividing the parasitic element 102.

Figure 24A:
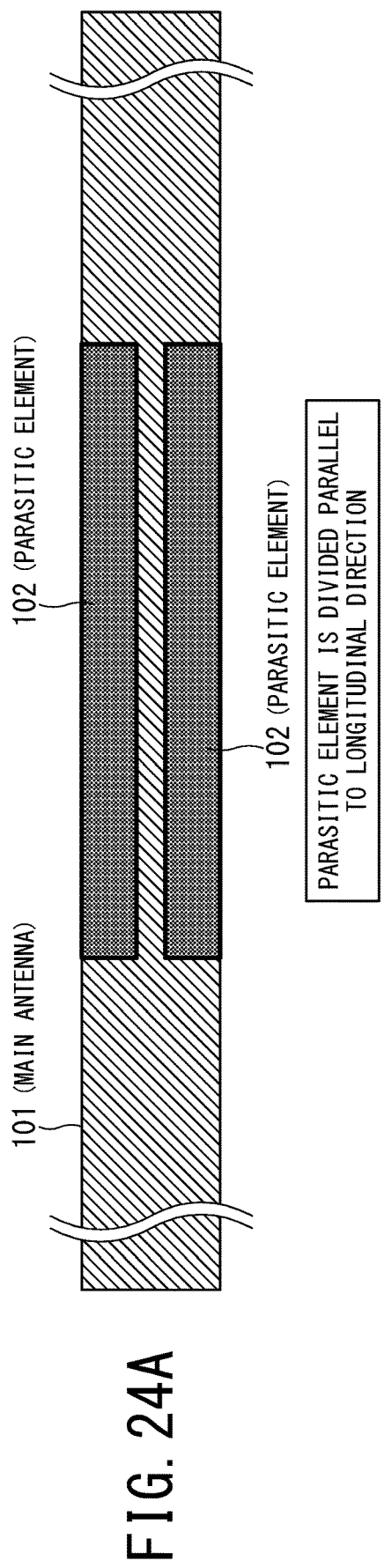
FIG. 24A and FIG. 24B are a top view and a circuit diagram for illustrating that the frequency characteristic of the antenna can be adjusted by dividing the parasitic element in the longitudinal direction.
Figure 24B:
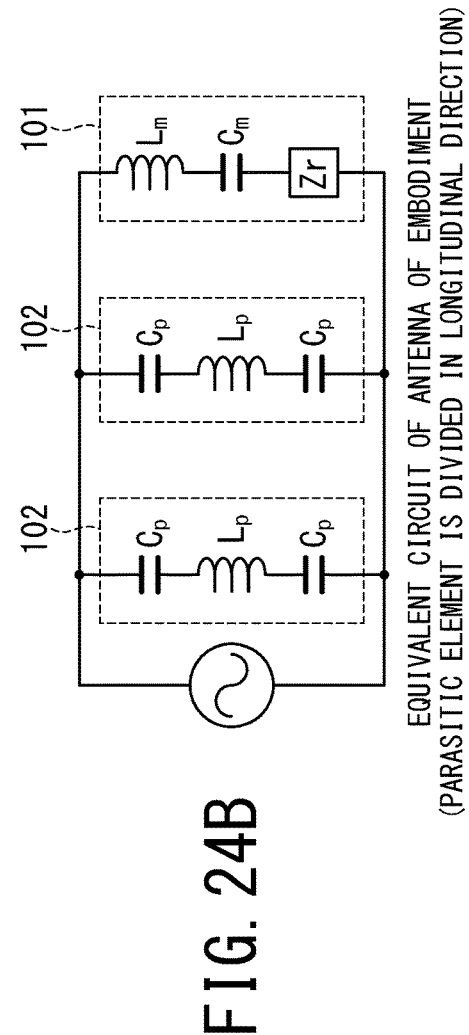

FIG. 24A and FIG. 24B are a top view and a diagram of an equivalent circuit for illustrating that the frequency characteristic of the antenna can be adjusted by dividing the parasitic element 102 into a plurality of divisions in the direction parallel to the longitudinal direction of the main antenna 101. When the parasitic element 102 is divided in the longitudinal direction, the equivalent circuit of the parasitic element 102 defined by the series resonant circuit of the capacitor Cp and the inductor Lp is added in parallel to the equivalent circuit of the main antenna 101 defined by the capacitor Cm, the inductor Lm, and the radiation resistor Zr. For example, when the parasitic element 102 is divided into two in the longitudinal direction as illustrated in FIG. 24A and FIG. 24B, the two equivalent circuits corresponding to the two divided parasitic elements 102 are added in parallel to the equivalent circuit of the main antenna 101. The number of equivalent circuits to be added increases or decreases depending on the number of divisions, and thus, the frequency characteristics can be adjusted with a high degree of freedom depending on the number of divisions in the longitudinal direction.

Figure 25A:
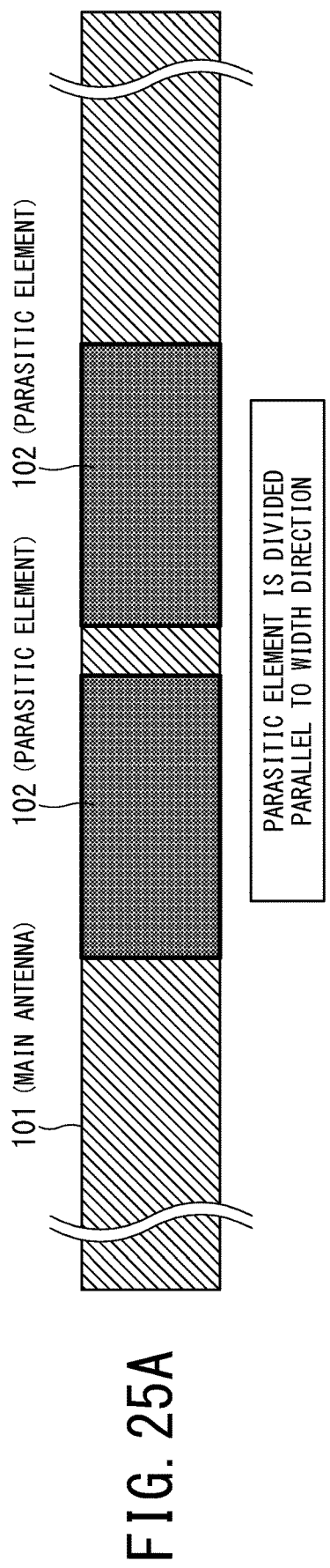
FIG. 25A and FIG. 25B are a top view and a circuit diagram for illustrating that the frequency characteristic of the antenna can be adjusted by dividing the parasitic element in the width direction.
Figure 25B:
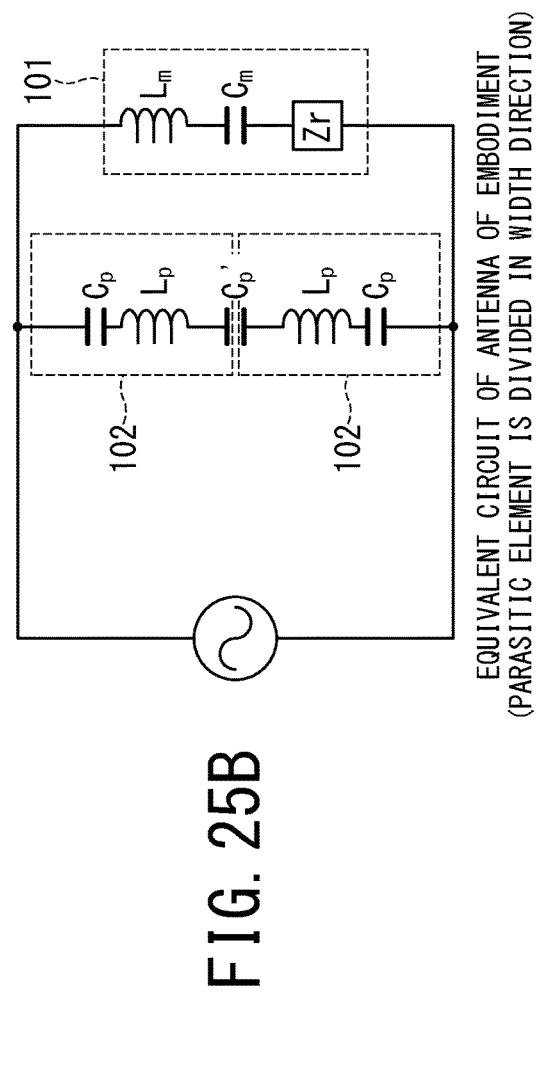

FIG. 25A and FIG. 25B are a top view and a diagram of an equivalent circuit for illustrating that the frequency characteristic of the antenna 10 can be adjusted by dividing the parasitic element 102 into a plurality of divisions in the direction parallel to the width direction of the main antenna 101. When the parasitic element 102 is divided in the width direction, the equivalent circuits of the parasitic element 102 defined by the series resonant circuit of the capacitor Cp and the inductor Lp are connected in series by the number corresponding to the number of divisions. The equivalent circuits of the parasitic element 102 connected in series is added in parallel to the equivalent circuit of the main antenna 101 defined by the capacitor Cm, the inductor Lm, and the radiation resistor Zr. For example, when the parasitic element 102 is divided into two in the width direction as illustrated in FIG. 25A and FIG. 25B, the two equivalent circuits corresponding to the two divided parasitic elements 102 are connected in series via the capacitor Cp', and the two equivalent circuits of the parasitic element 102 connected in series are added in parallel to the equivalent circuit of the main antenna 101. The divided parasitic elements 102 are capacitively coupled to each other, but the capacitor Cp' corresponds to the coupling capacitance between the two parasitic elements 102. In this manner, the number of equivalent circuits to be added increases or decreases depending on the number of divisions even by the division in the width direction, and thus, the frequency characteristics can be adjusted with a high degree of freedom depending on the number of divisions in the width direction.

Figure 26A:
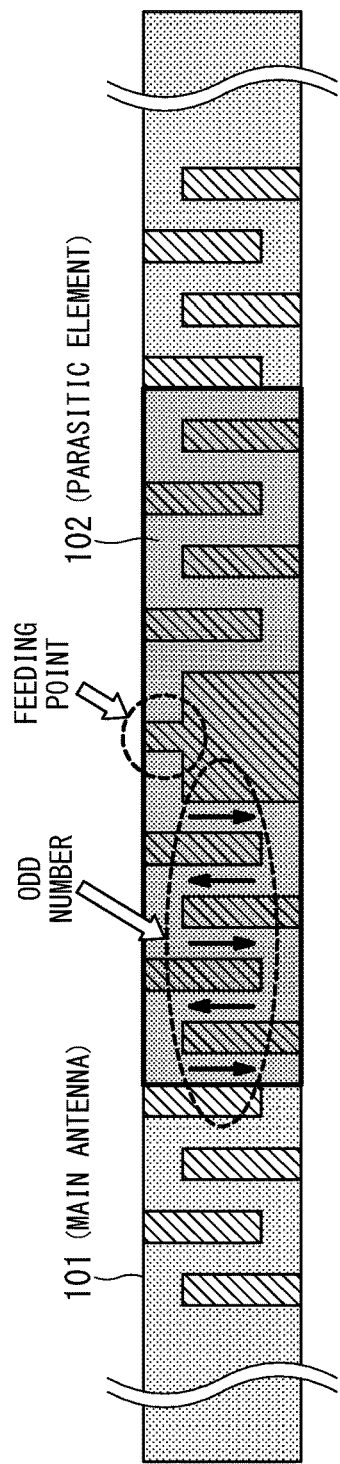
FIG. 26A to FIG. 26C are schematic top views illustrating a restriction condition between the parasitic element and the meander shape.
Figure 26B:
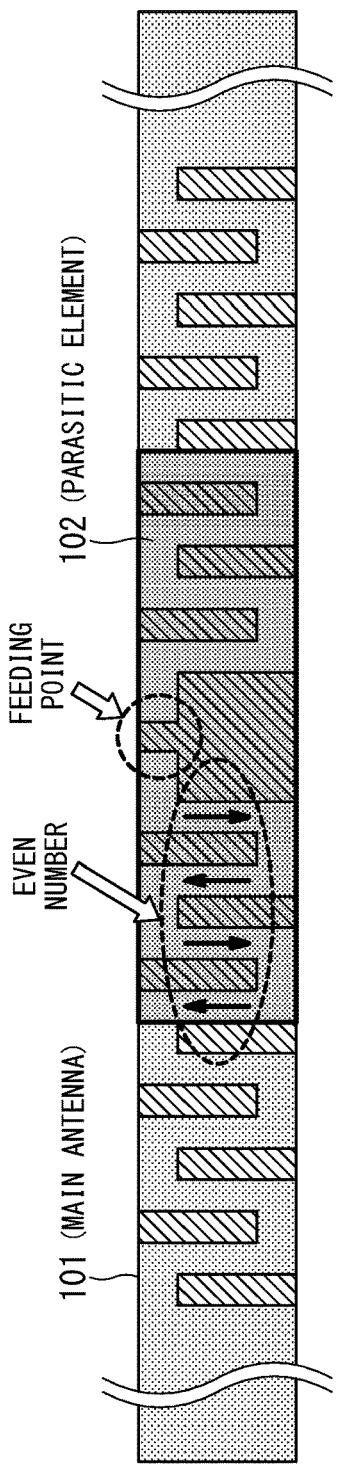
Figure 26C:
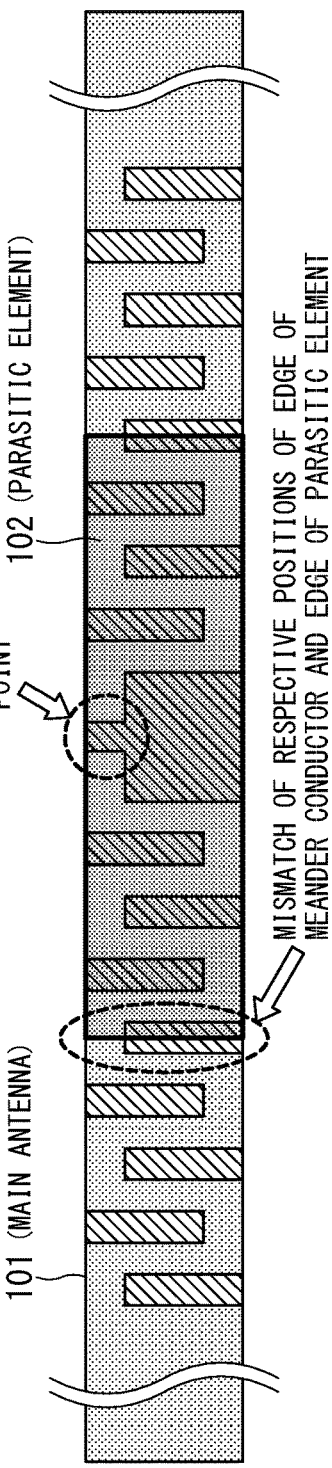

FIG. 26A to FIG. 26C are schematic top views illustrating a restriction condition between the parasitic element 102 and the meander-shaped region when the main antenna 101 is configured as a planar dipole antenna which central portion is formed of a meander-shaped conductor. In order to readily understand the positional relation between the parasitic element 102 on the top face and the meander-shaped conductor on the bottom face of the substrate 110 of the main antenna 101, FIG. 26A to FIG. 26C are illustrated as virtual top views in which the top and bottom faces are virtually overlayed by virtually making the meander-shaped conductor pattern transparent through the substrate 110. In the region of the meander-shaped conductor, as described above, the thin conductor is bent into a crank shape a plurality of times.

As shown in FIGS. 22A to 22C, the main antenna 101 is configured as a planar dipole antenna, and both regions from a feeding point 110 of the planar dipole antenna to predetermined positions toward both ends of the main antenna 101 are formed as a meander line in which a conductor is provided as a plurality of such that the meander line comprises a plurality of conductor sections that extend across a width of the planar dipole antenna.

The conductor (111, 112) is formed as a solid-pattern in both regions from the predetermined positions to the both ends, and the parasitic element 102 is rectangular having a long side in a longitudinal direction of the planar dipole antenna and a short side in a width direction of the planar dipole antenna such that the parasitic element 102 is overlaid on the meander line in the width direction and is partially overlaid on the meander line in the longitudinal direction.

Here, note that, as shown in FIG. 26A, the parasitic element 102 is provided such that the parasitic element 102 overlies an odd number of the conductor sections, that extend across the width of the planer dipole antenna, in each of two regions from the feeding point to both ends of the antenna element.

It is unpreferable that the parasitic element 102 is overlaid through the meander-shaped region in such a manner that the number of the thin conductors arranged in the width direction is even (four in the case of FIG. 26B) in each of the two regions from the feeding point to both ends of the antenna element. Conversely, as shown in FIG. 26A, it is preferred that the parasitic element 102 is overlaid through the meander-shaped region in such a manner that the number of the thin conductors arranged in the width direction is odd (five in the case of FIG. 26A) in each of the two regions from the feeding point to both ends of the antenna element. The reason is as follows. When the number of the thin conductors arranged in the width direction is even, the electric field component due to the thin conductors is canceled, the capacitor component becomes smaller, and the effect of the parasitic element 102 is reduced. When the number of the thin conductors arranged in the width direction is an odd number, the capacitor component can be increased and the effect of the parasitic element 102 can be maintained.

In terms of the positions of both ends of the parasitic element 102 in the longitudinal direction, the parasitic element 102 is desirably formed in a manner as shown in FIG. 26A. Specifically, the position of an outer edge of the outermost thin conductor of the meander-shaped conductor preferably matches the position of the outer edge of the parasitic element 102, in a longitudinal direction.

In other words, it is preferable that the position of an outer edge of an outermost one of the conductor sections, that extend across the width of the planer dipole antenna, substantially matches a position of an outer edge of the parasitic element 102, in the longitudinal direction.

By contrast, as shown in FIG. 26C, it is unpreferable that the outer edge of the outermost thin conductor of the meander-shaped conductor and the outer edge of the parasitic element 102 do not positionally match. For example, in a case where the position of the outer edge of parasitic element 102 is between the outer and inner edges of the outermost thin conductor as shown in FIG. 26C, even a small change in the positional relation between the outer edge of the parasitic element 102 and the outer edge of the thin conductor may cause a large change in the electric field component, and may increase the possibility that the frequency characteristic of the antenna 10 significantly changes. As a result, individual difference in frequency characteristic of the antenna 10 becomes large due to manufacturing errors of the parasitic element 102 and the main antenna 101, which is not preferable. When the position of the outer edge of the thin conductor and the position of the outer edge of the parasitic element 102 are matched, such inconvenience can be avoided and variations in frequency characteristics of the antenna 10 between individuals can be reduced.

FIG. 27A is a top view illustrating an appearance and a configuration of the antenna 10 of the third embodiment. FIG. 27B and FIG. 27C are a bottom view and a side view of the antenna 10 of the third embodiment, respectively. As shown in the side view of FIG. 27C, in the main antenna 101 of the antenna 10 of the third embodiment, a pair of rectangular planar conductors 111 are formed on the respective top and bottom sides of the substrate 110 and a pair of planar conductors 112 are similarly formed on the respective top and bottom sides such that the feeding point is interposed between the two planar conductors 111 and the two planar conductors 112.

The parasitic element 102 is formed on the planar conductors 111 and 112 on the top side with an insulating layer 121 interposed therebetween. The above-described technical effects can also be obtained by the antenna 10 of the third embodiment.

So far, a description has been given of the cases where both of the main antenna 101 and the parasitic element 102 are formed into a rectangular shape in the above-descried embodiments. However, the shapes of the main antenna 101 and the parasitic element 102 are not limited to a rectangle.

For example, the main antenna 101 and the parasitic element 102 are arranged such that the main antenna 102 is provided in a first plane and the parasitic element 102 is provided in a second plane, and the first and second planes are parallel to each other. Then, the main antenna 101 may be formed so as to have a line-symmetrical shape with respect to the first intersection line between the first plane in which the main antenna 101 is provided and a third plane, the third plane passing through the feeding point and being perpendicular to the first plane. Additionally, the parasitic element 102 may be formed so as to have a line-symmetrical shape with respect to the second intersection line between the second plane in which the parasitic element 102 is provided and a fourth plane, the fourth plane passing through the feeding point and being perpendicular to the second face.

In other words, the main antenna 101 may be formed to be symmetric with respect to a third plane, the third plane passing through the feeding point and being perpendicular to the first plane, and the parasitic element 102 may be formed to be symmetric with respect to the third plane.

Such a line-symmetric shape or a plane-symmetric shape is preferred for the following reason. If the shapes of the main antenna 101 and the parasitic element 102 are asymmetrical on the left and right, the antenna is no longer symmetrical and difficult to match the characteristic impedance of the transmission line (typically 50 ohms), for example.

Figure 28A:
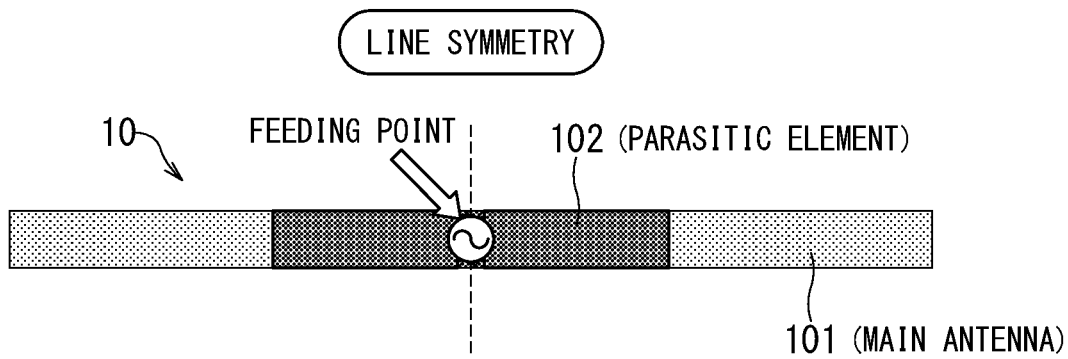
FIG. 28A to FIG. 28C are schematic diagrams illustrating some embodiments in which the respective shapes of the main antenna and the parasitic element are line-symmetrical with respect to the straight line including the feeding point.
Figure 28B:
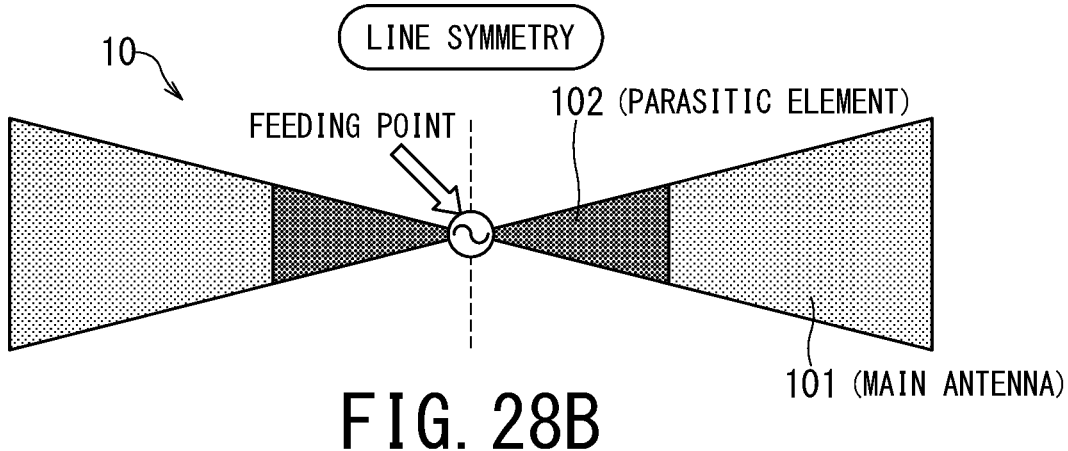
Figure 28C:
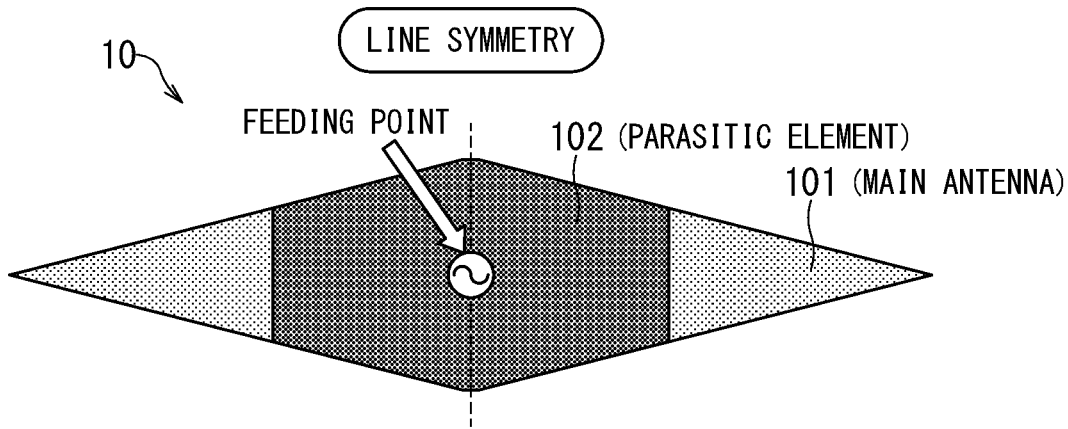

FIG. 28A to FIG. 28C are schematic diagrams illustrating embodiments in which the shapes of the main antenna 101 and the parasitic element 102 are line-symmetric as described above. In FIG. 28A to FIG. 28C, the meander-shaped conductor pattern is omitted. FIG. 28A illustrates a shape corresponding to the above-described first embodiment and second embodiment.

In FIG. 28B, the main antenna 101 is the antenna 10 of the embodiment configured as a so-called bow-tie antenna, and the shape of the parasitic element 102 is similar (i.e., homothetic) to the shape of the main antenna 101. FIG. 28C shows the antenna 10 in which the shape of the main antenna 101 is inverted from the shape of the bow-tie antenna and the base side of the isosceles triangle is used as the feeding point.

On the other hand, the main antenna 101 and the parasitic element 102 can be shaped as planar antennas that are point-symmetrical to the feeding point. In detail, the first face on which the main antenna 101 is disposed and the second face on which the parasitic element 102 is disposed are arranged so as to be parallel to each other, and then, the main antenna 101 can be formed to have a point-symmetrical shape with respect to a first intersection point of the first face on which the main antenna 101 is disposed and a first straight line including the feeding point and perpendicular to the first face on which the main antenna 101 is disposed. Additionally, the parasitic element 102 can be formed to have a point-symmetrical shape with respect to a second intersection point of the second face on which the parasitic element 102 is disposed and a second straight line including the feeding point and perpendicular to the second face on which the parasitic element 102 is disposed.

Figure 29A:
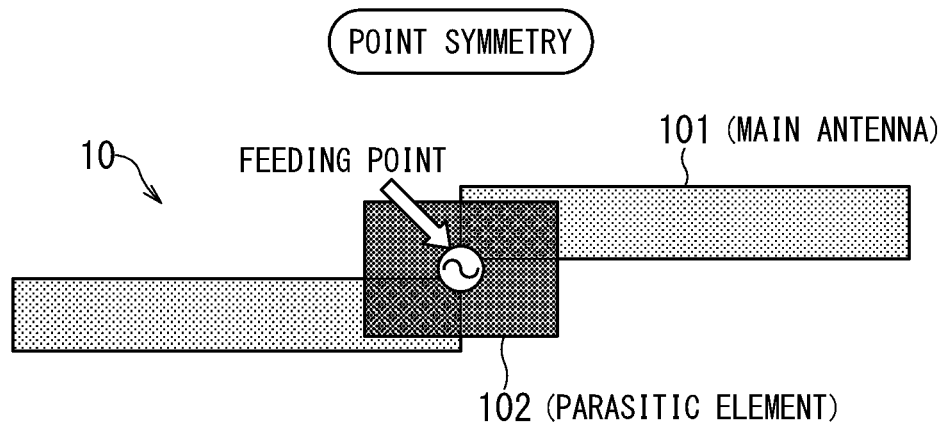
FIG. 29A and FIG. 29B are schematic diagrams illustrating embodiments in which the respective shapes of the main antenna and the parasitic element are point-symmetrical with respect to the feeding point.
Figure 29B:
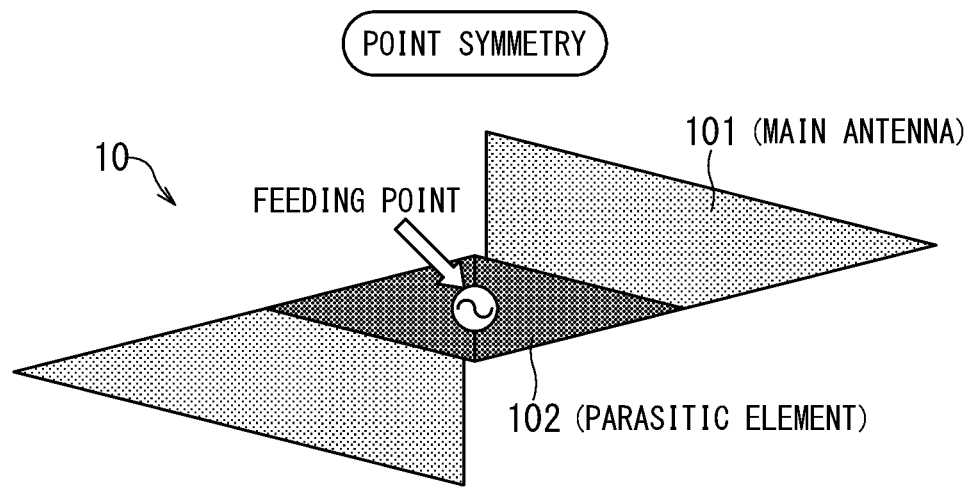

FIG. 29A and FIG. 29B are schematic diagrams illustrating embodiments in which the respective shapes of the main antenna 101 and the parasitic element 102 are point-symmetrical with respect to the feeding point. Also in FIG. 29A and FIG. 29B, the meander-shaped conductor pattern is omitted. FIG. 29A shows the antenna 10 in which the right and left antenna elements of a rectangular planar dipole antenna are arranged in a step-wise pattern, and this antenna 10 has a point-symmetrical shape with respect to the feeding point. The parasitic element 102 is disposed near the feeding point so as to cover the feeding point and be overlaid on the region near the feeding point of the right and left antenna elements. FIG. 29B shows the antenna 10 in which the right and left antenna elements in the shape of an isosceles triangle are arranged in a step-wise pattern, and the right and left antenna elements are arranged so as to be point-symmetrical with respect to the feeding point.

The antenna 10 of each of the above-described embodiments can have a wider bandwidth and be made smaller in size by adding the parasitic element 102 to the main antenna 101. Further, the biological information monitoring apparatus 1 using the antenna 10 of any one of the above-described embodiments can suppress the frequency shift of the antenna characteristics due to the respiratory motions and can reduce an influence of the respiratory motions that makes it difficult to detect the heartbeat.

According to the biological information monitoring apparatus 1 of each embodiment described above, biological information such as heartbeat and/or respiration of an object can be stably and highly reliably detected without imposing a burden on the object.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A biological information monitoring apparatus, comprising:
    an antenna assembly including at least one antenna, the antenna assembly being configured to be disposed adjacent to an object;
    a signal generator configured to generate a high-frequency signal; and
    a displacement detection circuit configured to detect a physical displacement of the object based on the high-frequency signal,
    wherein the at least one antenna comprises a main antenna to which the high frequency signal is supplied and a parasitic element to which the high frequency signal is not supplied,
    the main antenna is configured as a planar dipole antenna having a first face and a second face;
    the parasitic element is configured as a planar conductor mounted on one of the first and second faces of the planar dipole antenna in such a manner that the parasitic element is insulated from a conductor of the planar dipole antenna; and
    the at least one antenna, which has a circuit, is configured to cause a parallel resonance between the main antenna and the parasitic element,
    wherein the circuit of the at least one antenna comprises a first series resonant circuit and a second series resonant circuit are connected in parallel,
    in the first series resonant circuit, which corresponds to the main antenna, a first inductor and a radiation resistor are connected in series, and
    in the second series resonant circuit, which corresponds to the parasitic element, a second capacitor and a second inductor are connected in series.

2. The biological information monitoring apparatus according to claim 1, wherein the at least one antenna has a frequency characteristic that is wider in bandwidth than a frequency characteristic of the main antenna alone due to the parallel resonance.

3. The biological information monitoring apparatus according to claim 1, wherein:
    the parasitic element is arranged so as to be superimposed with a feeding point and a part of a region of the main antenna.

4. The biological information monitoring apparatus according to claim 1, wherein:
    the main antenna and the parasitic element are arranged such that the main antenna is provided in a first plane and the parasitic element is provided in a second plane, and the first and second planes are parallel to each other.

5. The biological information monitoring apparatus according to claim 4, wherein:
    the main antenna is formed to be line-symmetric with respect to a first intersection line between the first plane and a third plane, the third plane passing through a feeding point and being perpendicular to the first plane; and
    the parasitic element is formed to be line-symmetric with respect to a second intersection line between the second plane and a fourth face, the fourth plane passing through the feeding point and perpendicular to the second plane.

6. The biological information monitoring apparatus according to claim 4, wherein:
    the main antenna is formed to be point-symmetric with respect to a first intersection point of the first plane and a first straight line, the first straight line passing through a feeding point and being perpendicular to the first plane; and the parasitic element is formed to be point-symmetric with respect to a second intersection point of the second plane and a second straight line, the second straight line passing through the feeding point and being perpendicular to the second plane.

7. The biological information monitoring apparatus according to claim 1, wherein:
the at least one antenna is configured to be disposed adjacent to the object; and
the parasitic element is configured to be disposed on a face furthest from the object, of the first and second faces of the planar dipole antenna.

8. The biological information monitoring apparatus according to claim 1, wherein:
the conductor of the planar dipole antenna is formed into a meander shape in two regions from a feeding point to predetermined positions toward both ends of the main antenna, the feeding point being a point to be supplied with the high frequency signal; and
both of the two regions of the conductor from the predetermined positions to the both ends of the main antenna are formed as a solid-pattern.

9. The biological information monitoring apparatus according to claim 1, wherein the at least one antenna is adjustable by changing a shape and a size of the parasitic element.

10. The biological information monitoring apparatus according to claim 1, wherein:
the parasitic element is formed as a rectangular conductor that has a predetermined length in a longitudinal direction of the planar dipole antenna and has a predetermined width in a width direction of the planar dipole antenna.

11. The biological information monitoring apparatus according to claim 10, wherein the at least one antenna is adjustable in a frequency characteristic by changing a value of at least one of a length and a width of the parasitic element.

12. The biological information monitoring apparatus according to claim 10, wherein:
the parasitic element is divided into a plurality of divisions in a direction parallel to the longitudinal direction or in a direction parallel to the width direction; and
the at least one antenna is configured to be adjustable in frequency characteristic depending on number of the divisions of the parasitic element.

13. The biological information monitoring apparatus according to claim 1, wherein:
two regions from a feeding point of the planar dipole antenna to predetermined positions toward both ends of the main antenna are formed as a meander line in which the conductor is provided as a plurality of crank shapes such that the meander line comprises a plurality of conductor sections that extend across a width of the planar dipole antenna;
the conductor is formed as a solid-pattern in both of the two regions from the predetermined positions to the both ends;
the parasitic element is rectangular having a long side in a longitudinal direction of the planar dipole antenna and a short side in a width direction of the planar dipole antenna such that the parasitic element is overlaid on the meander line in the width direction of the planar dipole antenna and is partially overlaid on the meander line in the longitudinal direction of the planar dipole antenna; and
the parasitic element is provided such that the parasitic element aligns an odd number of the conductor sections, across the width of the planar dipole antenna, in each of two regions from the feeding point to both ends of the antenna element.

14. The biological information monitoring apparatus according to claim 1, wherein:
two regions from a feeding point of the planar dipole antenna to predetermined positions toward both ends of the main antenna are formed as a meander line in which the conductor is provided as a plurality of crank shapes such that the meander line comprises a plurality of conductor sections that extend across a width of the planar dipole antenna;
the conductor is formed as a solid-pattern in both of the two regions from the predetermined positions to the both ends;
the parasitic element is rectangular having a long side in a longitudinal direction of the planar dipole antenna and a short side in a width direction of the planar dipole antenna such that the parasitic element is overlaid on the meander line in the width direction of the planar dipole antenna and is partially overlaid on the meander line in the longitudinal direction of the planar dipole antenna; and
the parasitic element is provided such that a position of an outer edge of an outermost one of the conductor sections, that extend across the width of the planar dipole antenna, substantially matches a position of an outer edge of the parasitic element, in the longitudinal direction of the planar dipole antenna.

15. The biological information monitoring apparatus according to claim 1, further comprising a coupling amount detector configured to detect a coupling amount of a near-field coupling due to an electric field between the object and the at least one antenna.

16. The biological information monitoring apparatus according to claim 15, wherein
the high frequency signal generated by the signal generator is inputted to an input end of the at least one antenna, and the coupling amount detector is configured to detect a reflected signal as a S11 parameter, which is represented by the square root of the ratio of the reflected power to the input power that is inputted, indicating reflection loss of the at least one antenna, and detect the coupling amount of the near-field coupling based on the reflected signal, wherein the reflected signal is the high-frequency signal reflected from the input end of the at least one antenna.

17. The biological information monitoring apparatus according to claim 15, wherein,
the antenna assembly is configured to include a first antenna and a second antenna, the signal generator is configured to input the high frequency signal to the first antenna, and the coupling amount detector is configured to detect a transmitted signal as a S21 parameter indicating insertion loss from the first antenna to the second antenna and detect coupling amount of the near-field coupling on the basis of the transmitted signal, wherein the transmitted signal is the high-frequency signal that is inputted to the first antenna and then is transmitted through the second antenna.

18. A magnetic resonance apparatus, comprising the biological information monitoring apparatus according to claim 1.

* * * * *